US009856275B2

(12) United States Patent
Molander et al.

(10) Patent No.: US 9,856,275 B2
(45) Date of Patent: Jan. 2, 2018

(54) SYNTHESIS AND USE OF FLUORINATED COMPOUNDS

(71) Applicant: The Trustees of The University of Pennsylvania, Philadelphia, PA (US)

(72) Inventors: Gary Alan Molander, Broomall, PA (US); Oana Andreea Argintaru, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 14/767,103

(22) PCT Filed: Feb. 12, 2014

(86) PCT No.: PCT/US2014/016007
§ 371 (c)(1),
(2) Date: Aug. 11, 2015

(87) PCT Pub. No.: WO2014/126990
PCT Pub. Date: Aug. 21, 2014

(65) Prior Publication Data
US 2016/0002270 A1 Jan. 7, 2016

Related U.S. Application Data

(60) Provisional application No. 61/763,595, filed on Feb. 12, 2013, provisional application No. 61/897,371, filed on Oct. 30, 2013.

(51) Int. Cl.
| | | |
|---|---|---|
| C07F 5/04 | (2006.01) | |
| C07F 5/02 | (2006.01) | |
| C07C 17/263 | (2006.01) | |
| C07C 22/08 | (2006.01) | |
| C07C 67/343 | (2006.01) | |
| C07C 41/22 | (2006.01) | |
| C07C 41/26 | (2006.01) | |
| C07C 41/30 | (2006.01) | |
| C07B 39/00 | (2006.01) | |
| C07C 29/36 | (2006.01) | |
| C07D 209/08 | (2006.01) | |

(52) U.S. Cl.
CPC ............ C07F 5/04 (2013.01); C07B 39/00 (2013.01); C07C 17/263 (2013.01); C07C 22/08 (2013.01); C07C 29/36 (2013.01); C07C 41/22 (2013.01); C07C 41/26 (2013.01); C07C 41/30 (2013.01); C07C 67/343 (2013.01); C07D 209/08 (2013.01); C07F 5/02 (2013.01); C07B 2200/09 (2013.01)

(58) Field of Classification Search
CPC ...................................................... C07F 5/04
See application file for complete search history.

(56) References Cited

U.S. PATENT DOCUMENTS

| | | |
|---|---|---|
| 3,078,305 A | 2/1963 | Dobratz et al. |
| 3,287,391 A | 11/1966 | Towers et al. |
| 6,335,423 B1 | 1/2002 | Varma |
| 2008/0194500 A1 | 8/2008 | Mecozzi et al. |
| 2009/0238897 A1 | 9/2009 | Galic |
| 2010/0160683 A1 | 6/2010 | Matoba et al. |

OTHER PUBLICATIONS

DePuy, et al. Document No. 80:132409, retrieved from STN, 1974.*
Zakharov, et al. Document No. 85:176984; retrieved from STN, May 12, 1984.*
Barluenga et al, "Metal-Free Carbon-Carbon Bond-Forming Reductive Coupling Between Boronic Acids and Tosylhydrazones", Nature Chemistry, Sep. 2009, 1, 494-499.
Bawn et al, "The Mechanism of the Polymerization of Diazoalkanes Catalyzed by Boron Compounds", Journal of Polymer Science, 1959, XXXIv, 93-108.
Busch et al, "The Boron-Catalyzed Polymerization of Dimethylsulfoxonium Methylide. A Living Polymethylene Synthesis", Journal of the American Chemical Society, Apr. 10, 2002, 124(14), 3636-3646.
DeSimone et al, "Synthesis of Fluoropolymers in Supercritical Carbon Dioxide", Science, Aug. 14, 1992, 257(5072), 945-947.
Dhara, M.G. and Banerjee, S., "Fluorinated High-Performance Polymers: Poly(arylene ether)s and Aromatic Polyimides Containing Trifluoromethyl Group", Progress in Polymer Science, Aug. 2010, 35(8), 1022-1077.
Franssen et al, "Controlled Synthesis of Functional Copolymers with Blocky Architectures via Carbene Polymerization", Macromolecules, 2012, 45, 3711-3721.
Genzer et al, "The Orientation of Semifluorinated Alkanes Attached to Polymers at the Surface of Polymer Films", Macromolecules, 2000, 33(5), 1882-1887, Published Online: Feb. 15, 2000.
Ihara et al, "Polymerization of Various Alkyl Diazoacetates Initiated with (N-Heterocyclic Carbene)Pd/Borate Systems", Macromolecules, 2011, 44(9), 3287-3292, Publication Online: Apr. 4, 2011.
International Application No. PCT/US14/16007: International Search Report and The Written Opinion dated May 15, 2014, 34 pages.

(Continued)

*Primary Examiner* — Shawquia Jackson
(74) *Attorney, Agent, or Firm* — Baker & Hostetler LLP

(57) ABSTRACT

The invention is directed to the preparation of fluorinated compounds and their use in organic synthesis. In particular, the invention is directed to methods of reacting compounds of structure with $R_f$—CH=$N_2$ or $(CF_3)_2C$=$N_2$ to form a perfluoroalkylate or -arylated compounds, and products derived from these reactions, where X, $Y_B$, and $R_f$ are described herein.

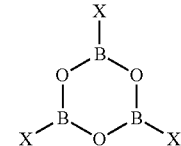

18 Claims, 6 Drawing Sheets

(56) References Cited

OTHER PUBLICATIONS

Jellema et al, "CI Polymerisation and Related C—C Bond Forming 'Carbene Insertion' Reactions", Chemical Society Reviews, May 2010, 39(5), 1706-1723.

Jellema et al, "Rh-Mediated Polymerization of Carbenes: Mechanism and Stereoregulation", Journal of the American Chemical Society, Sep. 19, 2007, 129(37), 11631-11641.

Kato et al, "Surface Characterization of Poly(styrene-co-fluoroalkylfumarate): XPS and Contact Angle Measurement Study", Journal of Applied Polymer Science, Feb. 14, 1999, 71(7), 1049-1054.

Li et al, "Trasition-Metal-Free Synthesis of Pinacol Alkylboronates From Tosylhydrazones", Angewandte Chemie International Ed., Mar. 19, 2012, 51(12), 2943-2946.

Liu et al, "Novel Anionic Fluorine-Containing Amphiphilic Self-Assembly Polymer Micelles for Potential Application in Protein Drug Carrier", Journal of Fluorine Chemistry, Sep. 2012, 141 21-28.

Luo, J. and Shea, K.J., "Polyhomologation. A Living C1 Polymerization", Accounts of Chem Ical Research, Nov. 16, 2010, 43(11), 1420•1433.

Ma, J. and Cahard, D. "Strategies for Nucleophilic, Electrophilic, and Radical Trifluoromethylations", Journal of Fluorine Chemistry, 128, 2007, 975-996.

Molander et al, "Efficient Hydrolysis of Organotrifluoroborates via Silica Gel and Water", Journal of Organic Chemistry, Oct. 2, 2009, 74(19), 7364-7369.

Molander et al, "Preparation and Wittig Reactions of Organotrifluoroborato Phosphonium Viides", Organic Letters, 9(5), Mar. 1, 2007, 821-824.

Morandi, B. and Carreira, E., Synthesis of Trifluoroethyl-Substituted Ketones From Aldehydes and Cyclohexanones, Angewandte Chemie International. ed., Sep. 19, 2011, 50(39), 9085-9088.

Nave et al, "Protodeboronation of Tertiary Boronic Esters: Asymmetric Synthesis of Tertiary Alkyl Stereogenic Centers", Journal of American Chemical Society, Nov. 2010, 132(48), 17096-17098.

Park et al, "Synthesis of Fluorine-Containing Graft Copolymers of Poly(perfluoroalkylethyl methacrylate)-g-poly(methyl methacrylate) by the Macromonomer Technique and Emulsion Copolymerization Method", Polymer, 1997, 38(10), 2523-2527.

Perttu et al., The Synthesis and Characterization of Phenylacetylene A Tripodal Compounds Containing Boroxine Cores, Tetrahedron Letters, Dec. 12, 2005, 46(50), 8753-8756.

Perutz et al, "Synthesis and Surface Energy Measurement of Semi-Fluorinated, Low-Energy Surfaces", Macromolecules, 1998, 31(13), 4272-4276, Publication Online: Jun. 6, 1998.

Purser et al, "Fluorine in Medicinal Chemistry", Chemical Society Reviews, Feb. 2008, 37(2), 320-330.

Shea et al, "Polybomologation. A Living Polymethylene Synthesis", Journal of The American Chemical Society, 1997, 119(38), 9049-9050, Publication Online: Sep. 24, 1997.

Skorokhodov, S.S. and Krakovjak, M.D., "Polymerization of Diazoalkanes on Boron Compounds with Rearrangement", Journal Polymer Sciences, 1969, Part C, 22(2), 1139-1147, Publication Online: Mar. 13, 2007.

SuperHydrophobic Coating, Oleophobic Coating, Non-Stick Treatments, Aculon Performance Surface Solutions, www.aculon.com, © 2004-2015, 1 page.

Wu et al, "Recent Developments on the Trifluoromethylation of (Hetero)Arenes", Chemistry Asian Journal, 2012, 7, 1744-1754.

Zisman, W.A.,(Fowkes, F., Ed.) "In Contact Angle, Wettability, and Adhesion, Relation of the Equilibrium Contact Angle to Liquid and Solid Constitution", Jan. 1, 1964, 1-51.

\* cited by examiner

Antiretroviral agent

Efavirenz

HIV-1 Treatment

Antiosteoporotic agent

Odanacatib (MK-0822)

Cathepsin K inhibitor

- Cu-catalyzed borylation of alkyl electrophiles

~100 reactions using HTE

- Pd-catalyzed borylation of alkyl electrophiles

~200 reactions using HTE

SYNTHESIS AND USE OF FLUORINATED COMPOUNDS

CROSS-REFERENCE TO RELATED APPLICATIONS

This application is the National Stage of International Application No. PCT/US2014/016007, filed Feb. 12, 2014, which claims the benefit of U.S. Provisional Application No. 61/763,595, filed Feb. 12, 2013 and U.S. Provisional Application No. 61/897,371, filed Oct. 30, 2013, the entire disclosures of both of which are incorporated herein by reference.

GOVERNMENT RIGHTS

This invention was made with government support under Grant No. R01-GM-081376 awarded by the National Institutes of Health. The government has certain rights in the invention.

TECHNICAL FIELD

The invention is directed to the preparation of fluorinated compounds and their use in organic synthesis.

BACKGROUND

Fluorinated molecules are used in many applications, including medicinal chemistry and materials science (e.g., poly[tetrafluoroethylene] ("PTFE")). In medicinal chemistry, fluorine atoms have been incorporated in drugs for therapeutic use. See, e.g., FIG. 1. Although enormous synthetic efforts have been made to enable the facile and selective incorporation of polyfluorinated groups into organic molecules, the discovery of novel structural platforms is rare. In addition, many polyfluorinated materials have significant physical limitations, including insolubility and non-biodegradability.

Despite recent advances in organic synthesis, access to compounds trifluoromethylated at $sp^3$-hybridized carbon centers, and their derivatives, has been elusive.

SUMMARY

The present invention is directed to methods of preparing fluorinated products, said methods comprising reacting a reagent comprising a compound of Formula (II), or a compound of Formula (III)

$$X—Y_B \quad (II)$$

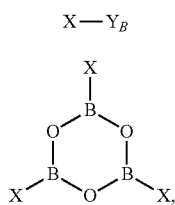

(III)

with $CF_3—CH=N_2$ to form an α-trifluoromethyl compound and optionally further reacting the α-trifluoromethyl compound with $KHF_2$, pinacol, an oxidizing reagent, or a protodeboronating agent under conditions sufficient to form a compound of Formula (I);

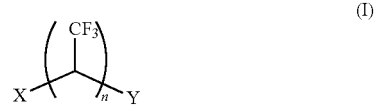

(I)

wherein
n is an integer from 1 to 50;
X is an optionally substituted $C_{1-20}$alkyl; optionally substituted $C_{1-20}$heteroalkyl; optionally substituted $C_{1-20}$alkenyl; optionally substituted cycloalkyl, optionally substituted heterocycloalkyl, optionally substituted aryl, optionally substituted heteroaryl, or fluorine; and
Y is H, —B-pinacol (or —BPin); —B(OR)$_2$; —BF$_3$K; —BZ$_2$; optionally protected —OH; —CH=CF$_2$; —NR$_2$; or —OC(O)R; optionally substituted $C_{1-20}$alkyl; optionally substituted aryl; optionally substituted heteroaryl; or halogen;
wherein each R is independently H or $C_{1-6}$alkyl;
wherein $Y_B$ is —B(OH)$_2$, —B(OR)$_2$, —BF$_3$K, or —BZ$_2$; and wherein each Z is independently Br, Cl, or F, and
when $Y_B$ is —BF$_3$K, the reaction further comprises reacting the compound of Formula (II) with a fluorophile prior to the reaction with $CF_3$—CH=N$_2$.
Additional embodiments provide that similar reactions are conducted with $R_f$—CH=N$_2$ (expanding from $CF_3$—CH=N$_2$) or $(CF_3)_2C$=N$_2$ to form a compound of Formula:

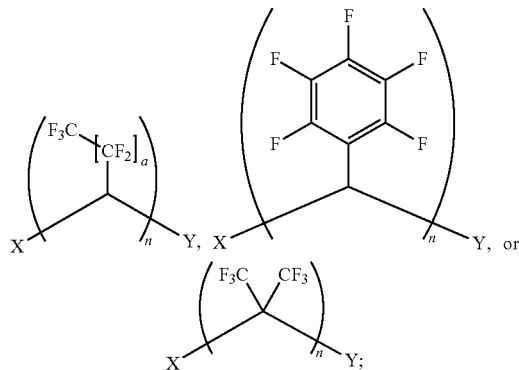

wherein
a is an integer from 0 to 6 or an integer from 1 to 6;
n is an integer from 1 to 50;
X is an optionally substituted $C_{1-20}$alkyl; optionally substituted $C_{1-20}$heteroalkyl; optionally substituted $C_{1-20}$alkenyl; optionally substituted cycloalkyl, optionally substituted heterocycloalkyl, optionally substituted aryl, optionally substituted heteroaryl, or fluorine; and
Y is H, —B-pinacol (or —BPin); —B(OR)$_2$; —BF$_3$K; —BZ$_2$; optionally protected —OH; —CH=CF$_2$; —NR$_2$; or —OC(O)R; optionally substituted $C_{1-20}$alkyl; optionally substituted aryl; optionally substituted heteroaryl; or halogen;
wherein each R is independently H or $C_{1-6}$alkyl;
wherein $R_f$ comprises —(CF$_2$)$_a$CF$_3$ or —C$_6$F$_5$;
wherein $Y_B$ is —B(OH)$_2$, —B(OR)$_2$, —BF$_3$K, or —BZ$_2$; and wherein Z is Br, Cl, or F, and
when $Y_B$ is —BF$_3$K, the reaction further comprises reacting the compound of Formula (II) with a fluorophile prior to the reaction with $R_f$—CH=N$_2$ or $(CF_3)_2C$=N$_2$.

Still further embodiments provide for fluorinated compounds, including the products of these methods. Such products may be described generally in terms of the structures:

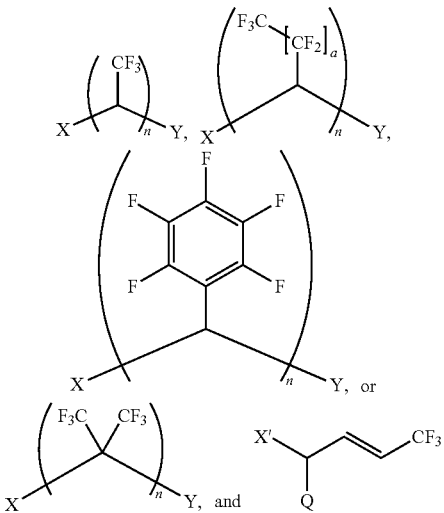

BRIEF DESCRIPTION OF THE DRAWINGS

The present application is further understood when read in conjunction with the appended drawings. For the purpose of illustrating the subject matter, certain exemplary embodiments are shown in the drawings; however, the presently disclosed subject matter is not limited to the specific methods, processes, schemes, and compounds disclosed.

DETAILED DESCRIPTION OF ILLUSTRATIVE EMBODIMENTS

Figure 1:
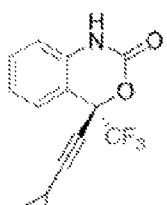
FIG. 1 provides the structures of two pharmaceutical compounds comprising an α-trifluoromethyl moiety that could be accessed using the compounds and methods of the invention.
Figure 1:
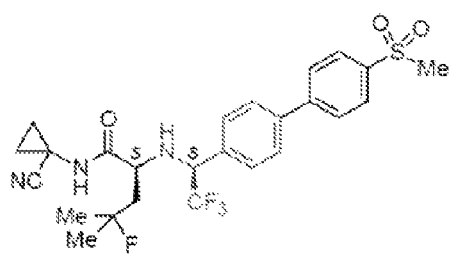

The present invention may be understood more readily by reference to the following description taken in connection with the accompanying Figures and Examples, all of which form a part of this disclosure. It is to be understood that this invention is not limited to the specific products, methods, processes, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this specification, claims, and drawings, it is recognized that the descriptions refer to compositions and processes of making and using said compositions. That is, where the disclosure describes or claims a feature or embodiment associated with a composition or a method of making or using a composition, it is appreciated that such a description or claim is intended to extend these features or embodiment to embodiments in each of these contexts (i.e., compositions, methods of making, and methods of using).

When a value is expressed as an approximation by use of the descriptor "about," it will be understood that the particular value forms another embodiment. In general, use of the term "about" indicates approximations that can vary depending on the desired properties sought by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

The present invention is directed to fluorinated organic compounds of Formula (Ia):

(Ia)

n is an integer from 1 to 50;
X is optionally substituted C$_{2-20}$alkyl; optionally substituted C$_{1-20}$heteroalkyl; optionally substituted C$_{2-20}$alkenyl; optionally substituted $C_{2-20}$alkynyl; optionally substituted cycloalkyl, optionally substituted heterocycloalkyl, optionally substituted aryl, optionally substituted heteroaryl, or fluorine; and Y is H—B-pinacol; —B(OR)$_2$; —BF$_3$K; BZ$_2$; —OH; —CH=CF$_2$; —NR$_2$; or halogen; or Y is —B-pinacol; —B(OR)$_2$; —BF$_3$K; or BZ$_2$; or Y is H or —CH=CF$_2$ when n is 2 to 50;

wherein each R is independently H or $C_{1-6}$alkyl; and Z is halogen.

Preferably, the compounds of Formula I are obtained in isolated form, that is, substantially free from a reaction mixture and substantially free of organic solvent and starting materials used to prepare the compounds of Formula (I). The compounds may be isolated individually, or may be contained within a mixture of compounds, including other compounds of Formula Ia.

In certain embodiments, n is an integer from 1 to 50. In other embodiments, n is 1 to 40 or n is 1 to 30. In still other embodiments, n is 1 to 20, 1 to 15, or 1 to 10. In certain of these embodiments, n is an integer from 1 to 5. In alternative embodiments, n is an integer from 6 to 10. In other embodiments, n is an integer from 11 to 50. In other embodiments, n is 2 to 50. In still other embodiments, n is 2 to 20, 2 to 15, or 2 to 10. Preferably, n is 1 or 2. In exemplary embodiments, n is 1. In other embodiments, n is 2.

In some embodiments, X is optionally substituted $C_{1-20}$alkyl, for example, optionally substituted methyl, ethyl, propyl, isopropyl, pentyl, butyl, and the like. In some embodiments, X is optionally substituted $C_{2-20}$alkyl, for example, optionally substituted ethyl, propyl, isopropyl, pentyl, butyl, and the like. In those embodiments where X is substituted $C_{1-20}$alkyl or $C_{2-20}$alkyl, the alkyl is substituted with 1, 2, or 3 substituents, each of which is independently selected from, for example, halogen, alkyl, haloalkyl; alkoxy, cycloalkyl, heterocycloalkyl, aryl, heteroaryl, phthalimide, —CN, —C(O)Oalkyl; —NO$_2$, —NH$_2$, —NH(alkyl), —N(alkyl)$_2$, —NHBoc, —SO$_2$alkyl, —SO$_2$aryl, —NHC(O)alkyl, or alkenyl.

In some embodiments, X is optionally substituted $C_{2-20}$alkenyl. In those embodiments where X is substituted $C_{2-20}$alkenyl, the alkenyl is substituted with 1, 2, or 3 substituents, each of which is independently selected from, for example, halogen, alkyl, haloalkyl, alkoxy, cycloalkyl, heterocycloalkyl, aryl, heteroaryl, phthalimide, —CN, —C(O)Oalkyl, NO$_2$, NH$_2$, NH(alkyl), N(alkyl)$_2$, NHBoc, SO$_2$alkyl, SO$_2$aryl, NHC(O)alkyl, or alkenyl.

In some embodiments, X is optionally substituted $C_{2-20}$alkynyl. In those embodiments where X is substituted $C_{2-20}$alkynyl, the alkynyl is substituted with 1, 2, or 3 substituents, each of which is independently selected from, for example, halogen, alkyl, haloalkyl, alkoxy, cycloalkyl, heterocycloalkyl, aryl, heteroaryl, phthalimide, —CN, —C(O)Oalkyl, NO$_2$, NH$_2$, NH(alkyl), N(alkyl)$_2$, NHBoc, SO$_2$alkyl, SO$_2$aryl, NHC(O)alkyl, or alkenyl.

In other embodiments, X is an optionally substituted aryl, for example, phenyl, naphthyl, or fluorenyl. In those embodiments where X is substituted aryl, the aryl is substituted with 1, 2, or 3 substituents, each of which is independently selected from, for example, halogen, alkyl, haloalkyl, alkoxy, cycloalkyl, heterocycloalkyl, aryl, heteroaryl, CN, —C(O)Oalkyl, NO$_2$, NH$_2$, NH(alkyl), N(alkyl)$_2$, NHBoc, SO$_2$alkyl, SO$_2$aryl, NHC(O)alkyl, or alkenyl. Preferably, the 1, 2, or 3 aryl substituents are independently selected from the group consisting of —OC$_{1-6}$alkyl; halogen; haloalkyl; —SO$_2$N(R$^1$)$_2$, wherein each R$^1$ is independently H or $C_{1-6}$alkyl; nitro, —OH, or —CN. Also preferred are those embodiments wherein the aryl substitutents are independently selected from the group consisting of $C_{1-6}$alkyl; $C_{1-6}$alkenyl; $C_{1-6}$alkynyl, —OC$_{1-6}$alkyl; —OC$_{1-6}$alkenyl; —C(O)C$_{1-6}$alkyl; —C(O)-aryl; —C(O)-heteroaryl; —C(O)OC$_{1-6}$alkyl; —C(O)O-aryl; —C(O)O-heteroaryl; —OC(O)C$_{1-6}$alkyl; —OC(O)-aryl; —OC(O)-heteroaryl; aryl; heteroaryl; halogen; CF$_3$; —SO$_2$N(R$^1$)$_2$, wherein each R$^1$ is independently H or $C_{1-6}$alkyl; nitro, —OH, or —CN.

In yet other embodiments, X comprises an optionally substituted heteroaryl. Preferred heteroaryl groups include furanyl, imidazolyl, pyrrolidinyl, pyrimidinyl, tetrazolyl, thienyl, pyridyl, pyrrolyl, N-methylpyrrolyl, quinolinyl, isoquinolinyl. In those embodiments where X is a substituted heteroaryl, the heteroaryl is substituted with 1, 2, or 3 substituents, each of which is independently selected from, for example, halogen, alkyl, haloalkyl, alkoxy, cycloalkyl, heterocycloalkyl, aryl, heteroaryl, CN, —C(O)Oalkyl, NO$_2$, NH$_2$, NH(alkyl), N(alkyl)$_2$, NHBoc, SO$_2$alkyl, SO$_2$aryl, NHC(O)alkyl, or alkenyl. Preferably, the heteroaryl group is substituted with substituents that are each independently selected from —OC$_{1-6}$alkyl; halogen; —CF$_3$; —SO$_2$N(R$^1$)$_2$, wherein R$^1$ is H or $C_{1-6}$alkyl; nitro, —OH, or —CN. In some embodiments, the heteroaryl is substituted with groups that are independently selected from $C_{1-6}$alkyl; —$C_{1-6}$alkenyl; —OC$_{1-6}$alkyl; —OC$_{1-6}$alkenyl; —C(O)C$_{1-6}$alkyl; —C(O)-aryl; —C(O)-heteroaryl; —C(O)OC$_{1-6}$alkyl; —C(O)O-aryl; —C(O)O-heteroaryl; —OC(O)C$_{1-6}$alkyl; —OC(O)-aryl; —OC(O)-heteroaryl; aryl; heteroaryl; halogen; CF$_3$; —SO$_2$N(R$^1$)$_2$, wherein each R$^1$ is independently H or $C_{1-6}$alkyl; nitro, —OH, or —CN.

Within the scope of the invention, the heteroaryl ring can be attached to Formula (I) through any available ring position.

In some embodiments of the invention, X is F.

Particularly preferred selections for X include, for example,

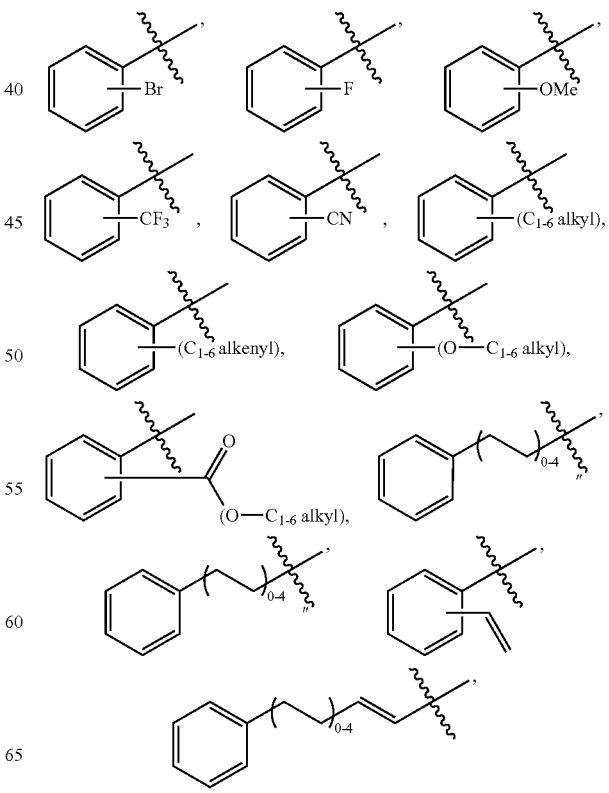

-continued

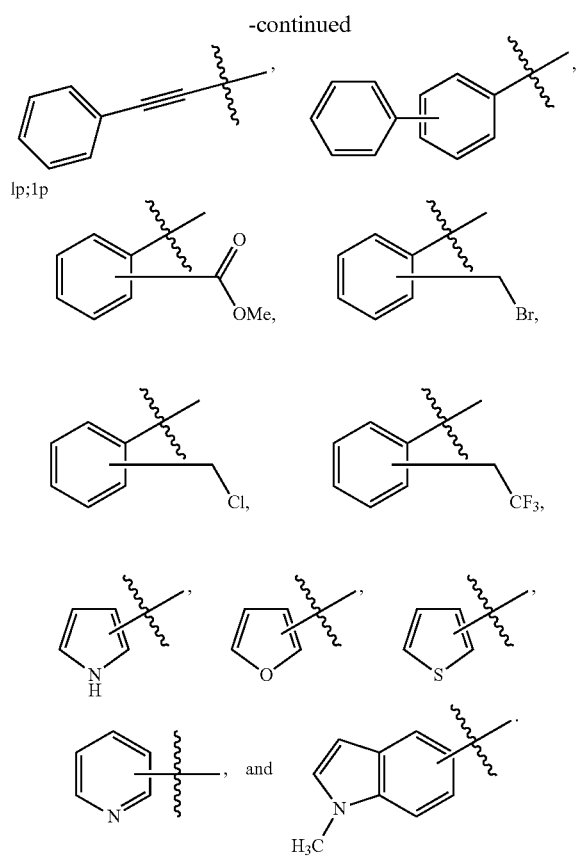

lp;1p

As is recognized by those skilled in the art, the descriptors provided above, in which each marker is presented to the center of the respective phenyl ring, connotes that the given substituent may be attached to any available carbon on that ring.

In some embodiments, Y is H.

In some preferred embodiments, Y is B-pinacol, that is,

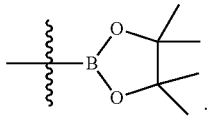 [SMILES: *B1OC(C)(C)C(C)(C)O1]

In some embodiments, Y is —B(OR)$_2$, wherein each R is independently H or C$_{1-6}$alkyl.

In still other embodiments, Y is —B(OH)$_2$.

In yet other embodiments, Y is —BF$_3$K, wherein K is potassium ion.

In other embodiments, Y is BZ$_2$, wherein Z is halogen.

In some embodiments, Y is —CH=CF$_2$.

In other embodiments, Y is —NR$_2$, wherein each R is independently H or —C$_{1-6}$alkyl.

In some embodiments, Y is —OH.

In some embodiments, Y is halogen.

In preferred embodiments, Y is —B(OR)$_2$, —B(OH)$_2$, —BF$_3$K, or OH. In yet other embodiments, Y is —B-pinacol, —B(OR)$_2$, —B(OH)$_2$, —BF$_3$K. In some embodiments, Y is —B(OR)$_2$, —B(OH)$_2$, —BF$_3$K. In other preferred embodiments, Y is H, —B(OR)$_2$, —B(OH)$_2$, —BF$_3$K, —CH=CF$_2$, or OH when n is 2 to 50.

When Y is —OH, it should be appreciated that additional embodiments include those where this functional group can be further derivatized using methods known in the art. For example, the —OH can be derivatized with a protecting group. Alternatively, the —OH moiety can be converted to, for example, an ether or ester moiety. Further examples of potential modifications are described herein.

As used herein, the α-position in the terms "α-trifluoromethyl," or corresponding α-perfluoroalkyl or -aryl refers to the position adjacent to the X group.

As used herein, "alkyl" refers to saturated, branched or unbranched, hydrocarbon groups, and can have a number of carbon atoms optionally designated (e.g., C$_{1-3}$ means one to three carbons). Preferably, the alkyl groups within the scope of the invention include from 1 to 20 carbons. Preferred alkyl groups include methyl, ethyl, propyl, isopropyl, butyl, isobutyl, tert-butyl, pentyl, isopentyl, hexyl, heptyl, and the like.

As used herein, "alkenyl" refers to straight chain or branched chain hydrocarbon groups including at least one carbon-carbon double bond. Preferably, alkenyl groups within the scope of the invention include from 2 to 20 carbons.

As used herein, "alkoxy" is used in its conventional sense, and refers to those alkyl groups attached to the remainder of the molecule via an oxygen atom. Alkoxy groups include, but are not limited to methoxy, ethoxy, and propoxy. Within the scope of the invention, "alkoxy" also encompasses haloalkoxy moieties, that is, alkoxy groups wherein at least one hydrogen of the alkyl portion has been replaced with one or more halogen. Examples of haloalkoxy moieties include trifluoromethoxy and difluoromethoxy.

As used herein, "cycloalkyl" refers to a saturated mono- or multicyclic ring system containing, for example, 3 to 10 carbon atoms. Such groups include, for example, cyclopropyl, cyclobutyl, cyclopentyl, and cyclohexyl.

As used herein, "heterocycloalkyl" refers to monocyclic, bicyclic, or multicyclic cycloalkyl groups, optionally fused to a phenyl ring, that include one, two or three heteroatoms independently selected from O, N, and S. Examples include tetrahydrofuranyl, pyranyl, morpholinyl, pyrrolidinyl, piperdinyl, morpholinyl, piperazinyl, phthalimide, and the like.

As used herein, "aryl" refers to aromatic moieties containing from 6 to 19 carbon atoms, present either as monocyclic or fused bicyclic or multicyclic groups. Aryl groups include, for example, fluorenyl, phenyl, and naphthyl.

The term "ester" refers to a chemical moiety with formula (R)$_n$COOR', where R and R' are independently selected from the group consisting of alkyl, cycloalkyl, aryl, heteroaryl (bonded through a ring carbon) and heteroalicyclic (bonded through a ring carbon), and where n is 0 or 1.

As used herein, an "ether" refers to an "—C—O—C—" group wherein either or both carbons may independently be part of an alkyl, alkenyl, alkynyl, aryl, heteroaryl or heteroalicyclyl group. A "halogenated ether" refers to an ether in which the groups to either side of the oxygen are both alkyl substituted with halogen.

As used herein, "heteroaryl" refers to a monocyclic, bicyclic, or multicyclic fused aromatic ring system wherein 1, 2, or 3 of the atoms in the ring is a heteroatom and the other atoms of the ring are carbon. Heteroatoms include, but are not limited to, nitrogen, oxygen, and sulfur. The heteroaryl group may be optionally fused to a benzene ring. In those embodiments including a nitrogen-containing heteroaryl moiety, the nitrogen can be substituted with —C$_{1-6}$alkyl, for example, N-methyl indole and N-methyl pyrrole.

As used herein, "halogen" refers to F, Cl, Br, or I.

As used herein, "haloalkyl" refers to an alkyl group wherein one or more of the hydrogens has been replaced with a halogen. Preferred haloalkyl groups include —CF₃, —CH₂Br, CH₂Cl, and the like.

The term "heteroalkyl," by itself or in combination with another term, means, unless otherwise stated, a stable straight or branched chain, or cyclic hydrocarbon group, or combinations thereof, consisting of a number of carbon atoms and at least one heteroatom selected from the group consisting of O, N, and S, and wherein the nitrogen, carbon and sulfur atoms may optionally be oxidized and the nitrogen heteroatom may optionally be quaternized. The heteroatom(s) O, N and S may be placed at any interior position of the heteroalkyl group or at the position at which the alkyl group is attached to the remainder of the molecule. Examples include, but are not limited to, —CH₂CH₂—O—CH₃, —CH₂CH₂—NH—CH₃, —CH₂CH₂—N(CH₃)—CH₃, —CH₂—S—CH₂CH₃, —CH₂CH₂—S(O)—CH₃, —CH₂CH₂—S(O)₂—CH₃, —CH=CH—O—CH₃, —CH₂—CH=N—OCH₃, and —CH=CH—N(CH₃)—CH₃. Up to two heteroatoms may be consecutive, such as, for example, —CH₂—NH—OCH₃.

As used herein, "Boc" represents tert-butoxycarbonyl (—C(O)—O-tBu).

In preferred embodiments, the recited alkyl, cycloalkyl, heterocycloalkyl, aryl, and heteroaryl groups may be optionally substituted. In such embodiments, there may be 1, 2, 3, or 4 substituents, independently selected from halogen, alkyl, cycloalkyl, heterocycloalkyl, aryl, heteroaryl, —CN, NO₂, NH₂, NH(alkyl), N(alkyl)₂, NHBoc, SO₂alkyl, SO₂aryl, NHC(O)alkyl, and alkenyl.

"Optional" or "optionally" means that the subsequently described circumstance may or may not occur, so that the description includes instances where the circumstance occurs and instances where it does not. For example, the phrase "optionally substituted" means that a given substituent may or may not be present.

"Hydroxyl protecting groups," are known in the art and include, for example, tetrahydropyranyl, 2-methoxypropyl, 1-ethoxyethyl, methoxymethyl, 2-methoxyethoxymethyl, methylthiomethyl, tert-butyl, tert-amyl, trityl, 4-methoxytrityl, 4,4'-dimethoxytrityl, 4,4',4"-trimethoxytrityl, benzyl, allyl, trimethylsilyl, (t-butyl)dimethylsilyl, and 2,2,2-trichloroethoxycarbonyl. The species of hydroxyl protecting groups is not critical so long as the derivatized hydroxyl group is stable to the conditions of subsequent reaction(s) and can be removed at the appropriate point without disrupting the remainder of the molecule. Further examples of hydroxy-protecting groups are described by C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3.

The terms "protodeboronation" and "protodeboronation agent" are known to those skilled in the art as reactions and reagents capable of replacing a boron moiety with a proton. As one example, tetrabutyl ammonium fluoride ("TBAF"), has been used for this purpose. Other protodeboronation agents will be understood to those of skill in the art.

To this point, the invention has been described in terms of its compounds, but it should be appreciated that the scope of the invention also includes methods for making these compounds. Certain embodiments provide methods of preparing compounds of Formula (I),

each method comprising reacting a compound of Formula (II) or Formula (III)

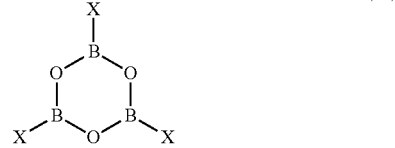

with CF₃—CH=N₂ and optionally, further reacting the trifluoromethyl compound with KHF₂, pinacol, an oxidizing reagent, or a protodeboronating agent under conditions sufficient to form a compound of Formula (I). Such conditions preferably include heating the reaction mixture. In these embodiments of the invention n is an integer from 1 to 50;

X is an optionally substituted $C_{1-20}$alkyl; optionally substituted $C_{1-20}$heteroalkyl; optionally substituted $C_{1-20}$alkenyl; optionally substituted cycloalkyl, optionally substituted heterocycloalkyl, optionally substituted aryl, optionally substituted heteroaryl, or fluorine; and Y is H, —B-pinacol (or —BPin); —B(OR)₂; —BF₃K; —BZ₂; —OH; —CH=CF₂; —NR₂; or —OC(O)R; optionally substituted $C_{1-20}$alkyl; or halogen;

wherein each R is independently H or $C_{1-6}$alkyl;

$Y_B$ is —B(OR)₂, —BF₃K, or —BZ₂; and wherein Z is Br, Cl, or F, and when $Y_B$ is —BF₃K, the reaction further comprises reacting the compound of Formula (II) with a fluorophile prior to the reaction with CF₃—CH=N₂.

While not intending to be necessarily bound by the correctness of any particular mechanism or theory, it appears that the reaction requires a substrate comprising a trivalent boron in order to effect the insertion of the diazocarbene. When Y is —BF₃K, the boron is tetravalent, and it is necessary to remove or at least labilize one of the fluorines, using a fluorophile, to provide the trivalent boron moiety. As used herein, the term "fluorophile" refers to a reagent or agent having an affinity for fluorine atoms, preferably capable of removing or labilizing a fluorine atom from boron. Exemplary fluorophiles include other boron compounds, such as BF₃, or silyl compounds such as Me₃SiCl (TMSCl), SiCl₄, MeSiCl₃, c-C₅H₉—SiCl₃, PhSiCl₃, or 4-Me-C₆H₄—SiCl₃.

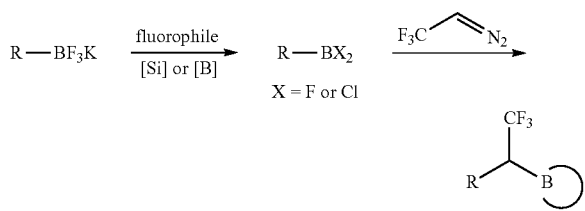

R = alkyl, alkenyl, alkynl, aryl, heteroaryl

Additional specific embodiments include those for preparing compounds having an aryl- or heteroaryl-α-trifluoromethyl group comprising reacting an aryl-B(OH)$_2$ or heteroaryl-B(OH)$_2$ with CF$_3$—CH=N$_2$ under conditions sufficient to form a trifluoromethyl-containing compound, wherein the aryl and heteroaryl are optionally substituted. Such methods may further comprise reacting the trifluoromethyl-containing compound with KHF$_2$, pinacol, an oxidizing reagent, or a protodeboronating agent to form the compound having an aryl- or heteroaryl-α-trifluoromethyl group; wherein the aryl and heteroaryl are optionally substituted.

When used, the CF$_3$—CH=N$_2$ is generated in situ, for example using the methods described herein. Further, certain embodiments provide that the reactions are done such that the molar ratio of boron to CF$_3$—CH=N$_2$ in a range of from about 1:1 to about 1:10, to about 1:20, or to about 1:100 or from about 1:11 to about 1:50, to about 1:100, or to about 1:200.

Still further embodiments include the specific methods described for making the compounds described herein, including permutations of such methods that would be obvious to those skilled in the art given the present teachings and the general knowledge in the art at the time of the filing of this application and its predecessor.

In certain embodiments, the CF$_3$—CH=N$_2$ or other diazomethane reactant is either prepared and isolated prior or generated in situ, prior to contacting with the remaining reactants. In other cases, the diazomethane is generated in situ in the presence of the other reactants.

Figure 2:
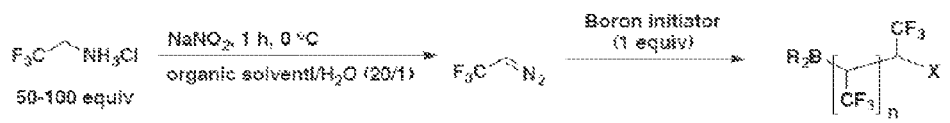
FIG. 2 is a schematic representation of a possible mechanism for the formation of compounds of the invention.
Figure 2:
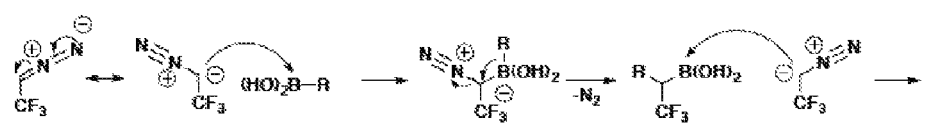
Figure 2:
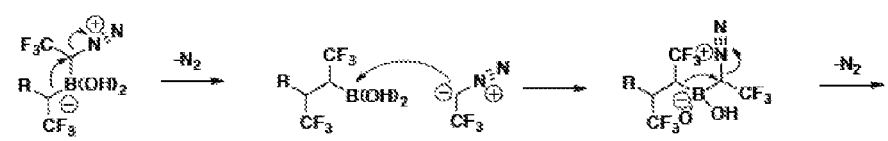
Figure 2:
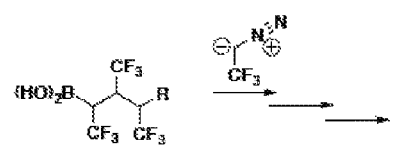

In certain embodiments, as described below, the reaction between the —B(OH)$_2$, —B(OR)$_2$, or —BZ$_2$ reactants and the CF$_3$—CH=N$_2$ (or other diazomethane) are conducted where the diazomethane is in excess, such that the ratio of the diazomethane to the boron-containing reactants is in a range of from about 1:1 to about 1:10. As is shown below, this generally, but not always, provides products in which n is 1 or 2. In other embodiments, the ratio of the diazomethane to the boron-containing reactants is 10 or greater, for example in a range of from about 10 to about 200, from about 10 to about 100, or from about 10 to about 50. In such cases, again as shown below, it is possible to prepare products where n is 3 or greater, for example up to about 10, 15, 20, 30, 40, or 50. While not intending to be bound by theory, this observation is at least consistent with the idea that the formation of oligomers or polymers are favored when there is sufficient excess diazomethane to allow for the insertion of this reactant into the first formed intermediate. FIG. 2 provides a schematic for a possible mechanism of this chain extension.

As described, the specific nature of Y can be effected by the presence or absence of KHF$_2$, pinacol, an oxidizing reagent, or a protodeboronating agent or by the application of heat (the latter favoring the formation of product where Y is —CH=CF$_2$, possibly owing to elimination reactions.

Figure 3A:
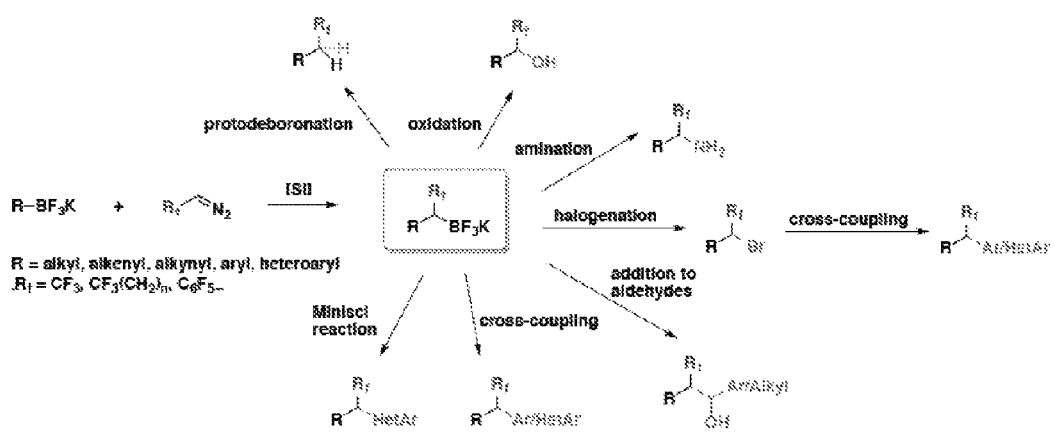
FIG. 3A illustrates options for further modifications of compounds and methods of the invention.
Figure 3B:
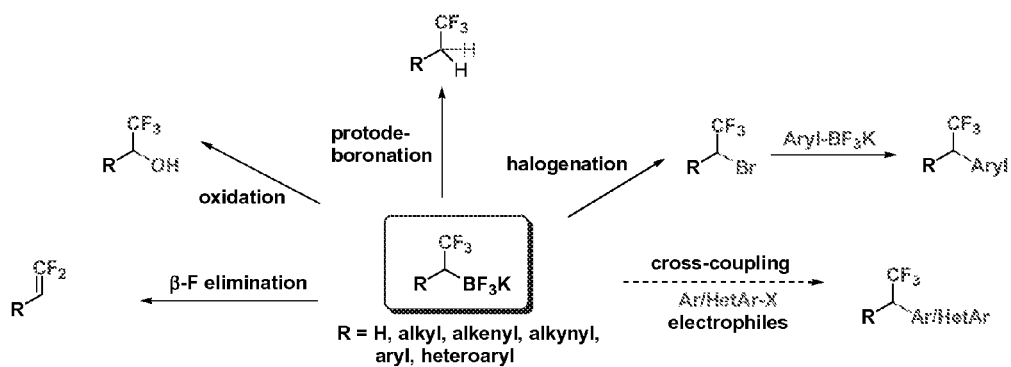
FIG. 3B illustrates complementary options for modifications for the compounds and methods of the invention.

It should also be recognized from the present teachings that products where Y is —B-pinacol (or —BPin); —B(OR)$_2$; —BF$_3$K; —BZ$_2$ (where R and Z are described above) may be converted to those where Y is hydrogen, halogen, optionally protected —OH, amine, optionally substituted aryl, or optionally substituted heteroaryl, using conventional transformational methods known to those skilled in the art—e.g., protodeboronation, oxidation, amination, halogenation, halogenation-cross-coupling, addition of aldehydes, or the Minisci reaction. See, e.g., FIG. 3A and FIG. 3B. Similarly, those products where Y is an optionally protected —OH may also be converted to an amine, cyano, ester, halogen, hydrogen, ketone, aryl or alkyl sulfonate ester, alkyl nitrate ester, alkylphosphate ester, optionally substituted aryl, or optionally substituted heteroaryl, also using conventional transformational methods known to those skilled in the art. Additionally, rearrangement or elimination reactions or both elimination and rearrangement reactions may be used to prepare additional compounds, such are described below. The products derived from each of these transformations are also considered within the scope of the present invention.

The compounds of the invention can be prepared according to the Schemes and experimental details provided herein, along with the skill in the art. For example, compounds of the invention, including compounds having an aryl- or heteroaryl-α-trifluoromethyl group, can be prepared by reacting an aryl-B(OH)$_2$ or heteroaryl-B(OH)$_2$ with CF$_3$—CH=N$_2$ to form a trifluoromethyl intermediate; and reacting the trifluoromethyl intermediate with KHF$_2$, pinacol, an oxidizing reagent, or a protodeboronating agent to form the compound having an aryl- or heteroaryl-α-trifluoromethyl group; wherein the aryl and heteroaryl are optionally substituted. Oligomers or polymers can be produced by following such a procedure. See, e.g., FIG. 2. As shown by the Examples below, when n is 2, the substituted perfluoro substituted azomethanes appear to add such that, where possible, the resulting pendant —CF$_3$, —(CF$_2$)$_n$CF$_3$, and perfluorophenyl appear to be arranged in syn-repeating units. It is understood that the insertion of consecutive stereocenters in the synthesis of oligomeric materials by the processes outlined has the possibility to generate stereoisomers, and these are within the scope of the invention.

Trifluoromethyl diazomethane (CF$_3$—CH=N$_2$) can be prepared according to method, for example, the sequence depicted in the following Scheme 1.

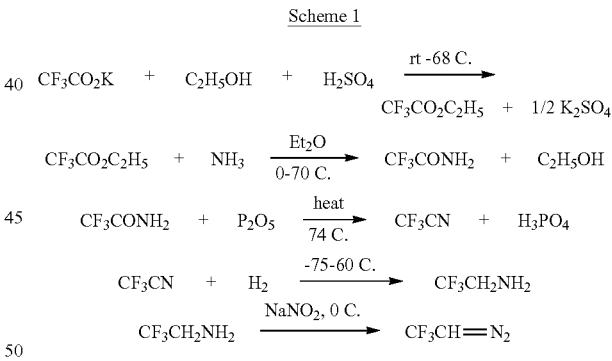

Scheme 1

While most of the discussion in the present disclosure relates to trifluoromethyl diazomethane (CF$_3$—CH=N$_2$), it should be appreciated that other substituted fluorinated diazoalkanes are useful and may be substituted in the present methods. That is, text describing an embodiment involving trifluoromethyl diazomethane or —CF$_3$ pendant should also be interpreted as describing the corresponding reagent provided below and perfluoroalkyl and -aryl pendants as separate embodiments. Such substituted fluorinated diazoalkanes are available according to the following Scheme:

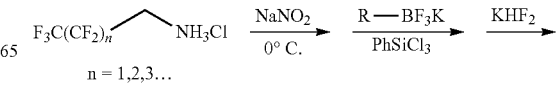

-continued

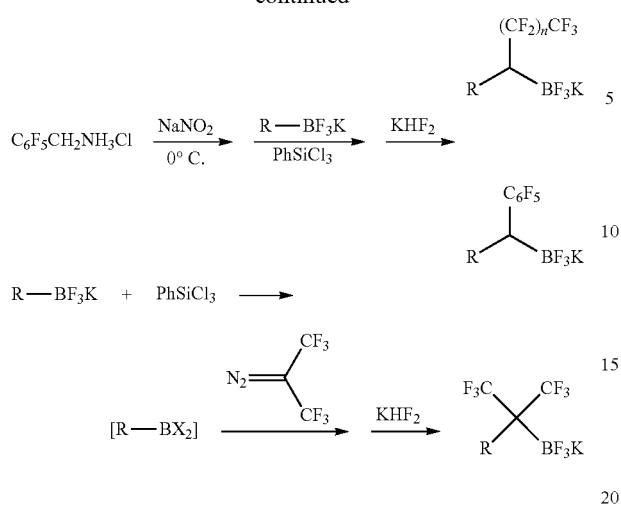

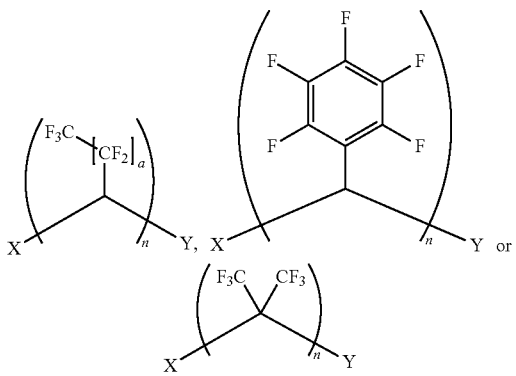

Accordingly, the compounds of the present invention may be more generally represented by the following formulae:

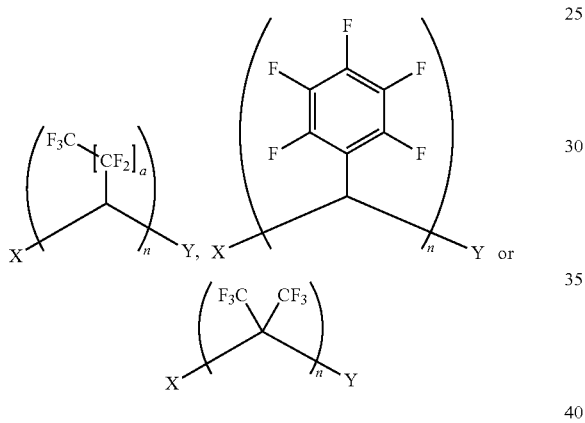

where a is an integer from 1 to 6. The syntheses used to prepare these compounds may also be seen as analogous to those described below, using these types of reagents.

For example, such methods may comprise reacting a reagent comprising a compound of Formula (II), or a compound of Formula (III)

$$X-Y_B \quad (II)$$

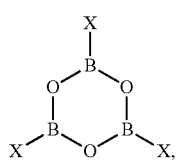
(III)

with $R_f\text{—CH}\!=\!\!N_2$ or $(CF_3)_2C\!=\!\!N_2$ to form an α-trifluoromethyl compound and optionally further comprising reacting the α-trifluoromethyl compound with $KHF_2$, pinacol, an oxidizing reagent, or a protodeboronating agent under conditions sufficient to form a compound of the following Formulae:

Preferably, the conditions for these methods include heating the reaction mixture. In these embodiments,
a is an integer from 0 to 6 or an integer from 1 to 6;
n is an integer from 1 to 50;
X is an optionally substituted $C_{1-20}$alkyl; optionally substituted $C_{1-20}$heteroalkyl; optionally substituted $C_{1-20}$alkenyl; optionally substituted cycloalkyl, optionally substituted heterocycloalkyl, optionally substituted aryl, optionally substituted heteroaryl, or fluorine; and
Y is H, —B-pinacol (or —BPin); —B(OR)$_2$; —BF$_3$K; —BZ$_2$; optionally protected —OH; —CH=CF$_2$; —NR$_2$; or —OC(O)R; optionally substituted $C_{1-20}$alkyl; optionally substituted aryl; optionally substituted heteroaryl; or halogen (preferably, Y is —B-pinacol; —B(OR)$_2$; —BF$_3$K; or BZ$_2$. In some embodiments, Y is —CH=CF$_2$ when n is 2 or more);
wherein each R is independently H or $C_{1-6}$alkyl;
wherein $R_f$ comprises —$(CF_2)_a CF_3$ or $C_6F_5$;
wherein $Y_B$ is —B(OH)$_2$, —B(OR)$_2$, —BF$_3$K, or —BZ$_2$; and wherein Z is Br, Cl, or F, and
when $Y_B$ is —BF$_3$K, the reaction further comprises reacting the compound of Formula (II) with a fluorophile prior to the reaction with $R_f$—CH=N$_2$ or $(CF_3)_2C$=N$_2$.

Trifluoromethyl-diazomethane can be reacted with boronic acids to produce compounds having an α-trifluoromethyl group, for example, as shown in the below Scheme 2. Particularly noteworthy is that the α-trifluoromethylated compounds are able to be isolated and are stable, in contrast to compounds previously described in the art.

Scheme 2

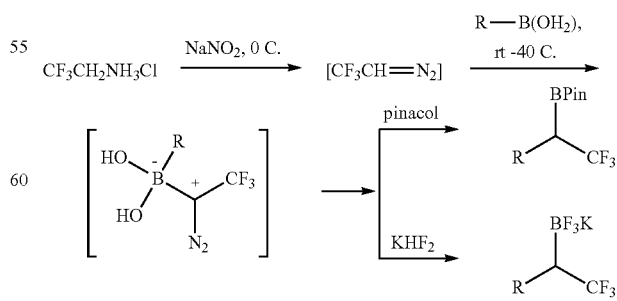

R is aryl, heteroaryl, alkyl, alkenyl

Exemplary examples of R in Scheme 2 include 4-methoxyphenyl, 3-chlorophenyl, 4-bromophenyl, and butyl, preferably n-butyl.

Also within the scope of the invention are methods of producing trifluoromethyl-substituted organotrifluoroborates by treating organotrifluoroborates with, for example, PhSiCl$_3$, p-tolylSiCl$_3$ and trimethylsilyl chloride, in the presence of CF$_3$CHN$_2$. Quenching the reaction mixture with KHF$_2$ provides the organotrifluoroborates. An exemplary sequence is set forth in Scheme 3.

Scheme 3

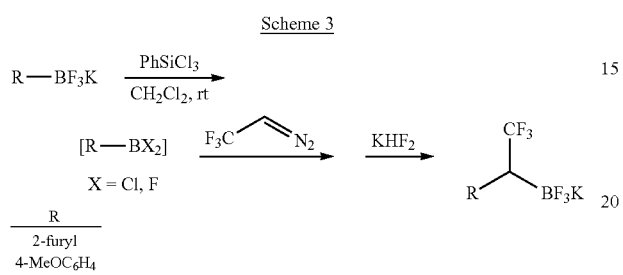

| R |
| --- |
| 2-furyl |
| 4-MeOC$_6$H$_4$ |

Additionally, arylboronic acid can be reacted with trifluoromethyl-diazomethane to produce a variety of aryl-α-trifluoromethyl-containing compounds, including organotrifluoroborates and alcohols. See, e.g., Scheme 4A.

Scheme 4A

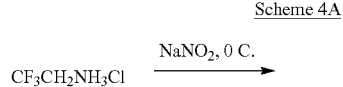

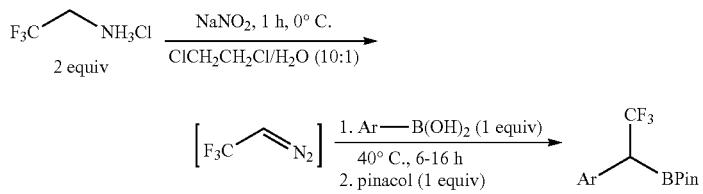

Figure 4:
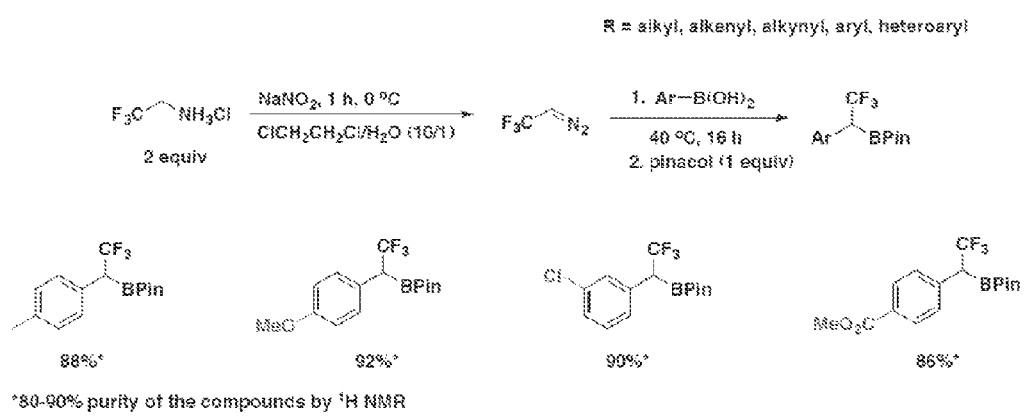
FIG. 4 are two schematic representations for syntheses of preferred aryl-B-pinacol ("BPin") and —BF$_3$K derivatives of the invention.
Figure 4:
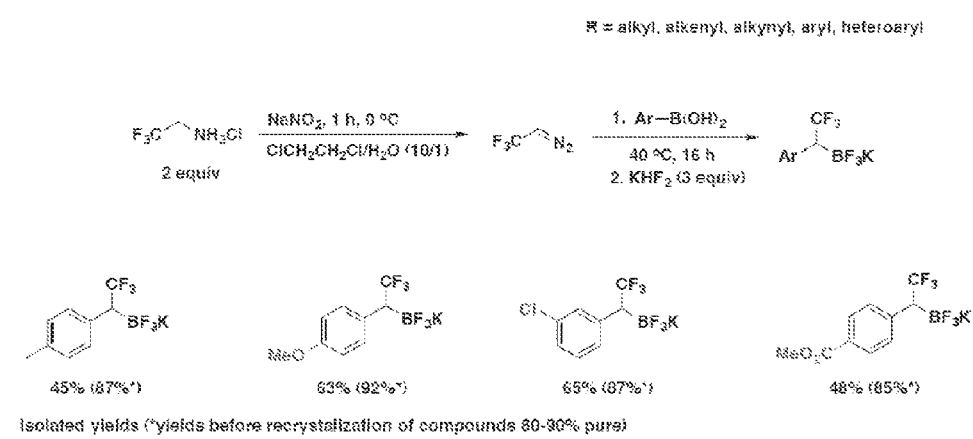
Figure 5:
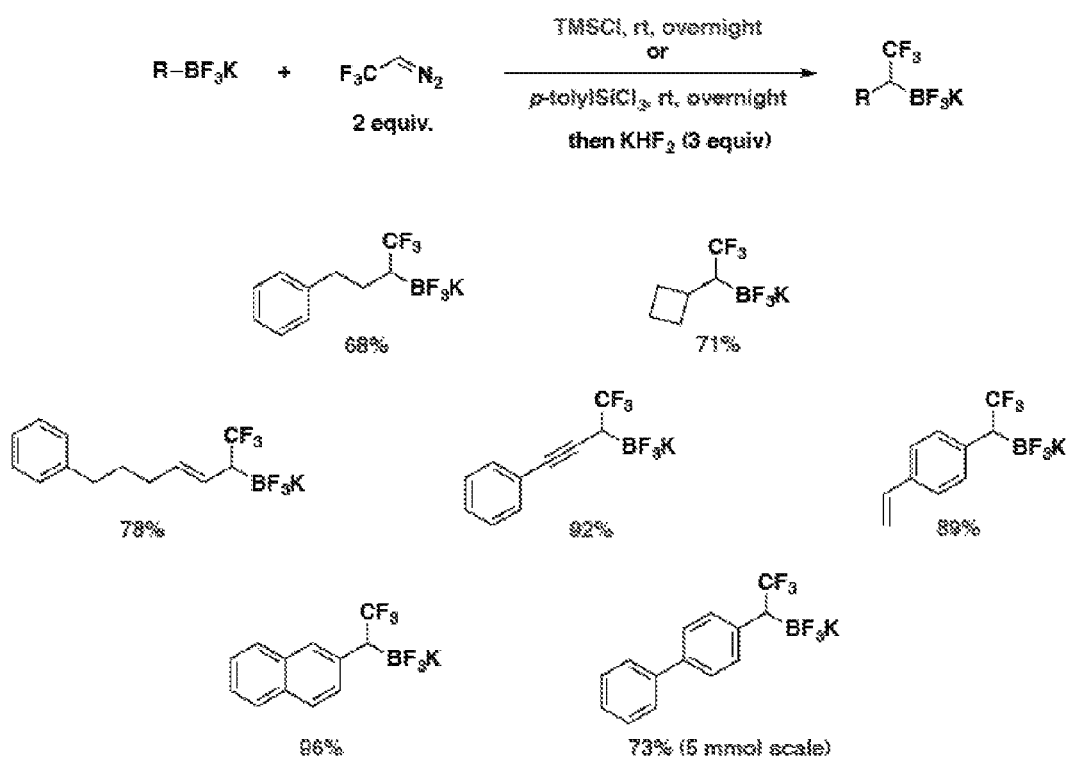
FIG. 5 is a schematic representation for the syntheses of preferred alkyl, cycloalkyl, allyl, propargyl, and aryl-BF$_3$K derivatives of the invention.
Figure 6:
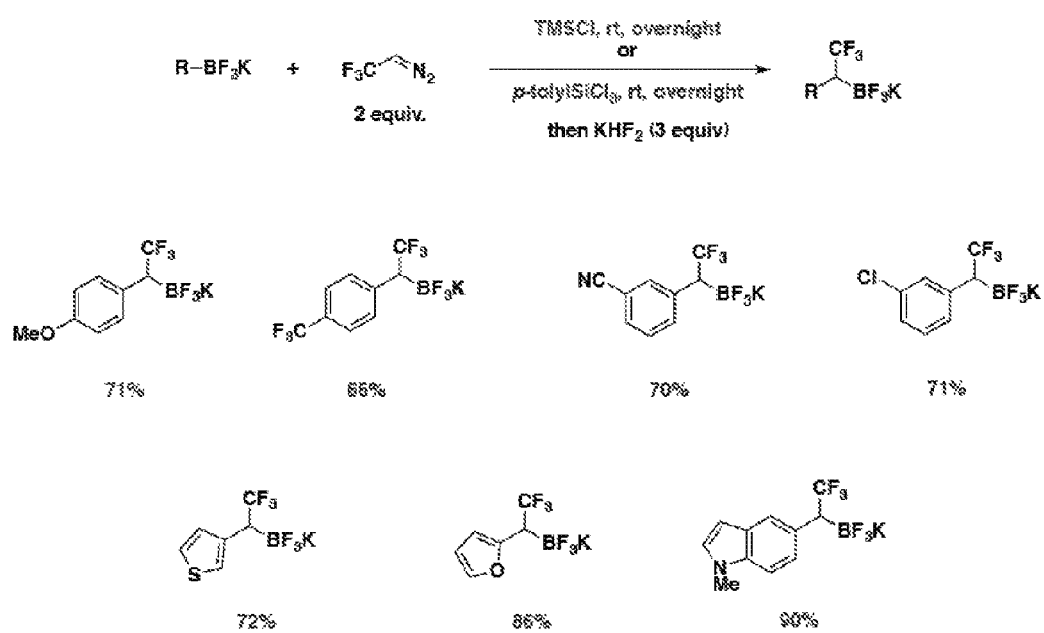
FIG. 6 is a schematic representation for the syntheses of preferred aryl- and heteroaryl-BF$_3$K derivatives the invention.

Compounds of the invention can also be prepared according to Schemes 4B (FIG. 4) and 4C (FIGS. 5 and 6):

Scheme 4B

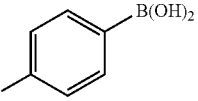

| substrate | product | % yield[a] |
| --- | --- | --- |
| 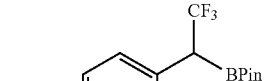 | 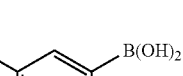 | 1a 73(38)[b] |
|  | 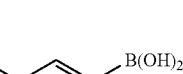 | 81 |
| 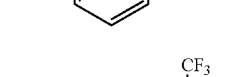 | 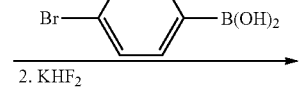 | 85 |

Scheme 4B

F₃C−CH₂−NH₃Cl (2 equiv) → [NaNO₂, 1 h, 0° C. / ClCH₂CH₂Cl/H₂O (10:1)] → [F₃C−CH=N₂] → 1. Ar−B(OH)₂ (1 equiv), 40° C., 6-16 h; 2. pinacol (1 equiv) → Ar−CH(CF₃)−BPin

| substrate | product | % yield[a] |
|---|---|---|
| 4-MeO₂C-C₆H₄-B(OH)₂ | 4-MeO₂C-C₆H₄-CH(CF₃)-BPin | 73 |
| 4-Me-C₆H₄-B(OH)₂ | 4-Me-C₆H₄-CH(CF3)-BPin | 80 |
| 4-MeO-C₆H₄-B(OH)₂ | 4-MeO-C₆H₄-CH(CF₃)-BPin | 1a 73(38)[b] |
| 3-Cl-C₆H₄-B(OH)₂ | 3-Cl-C₆H₄-CH(CF₃)-BPin | 81 |
| 3-NC-C₆H₄-B(OH)₂ | 3-NC-C₆H₄-CH(CF₃)-BPin | 85 |
| 4-MeO₂C-C₆H₄-B(OH)₂ | 4-MeO₂C-C₆H₄-CH(CF₃)-BPin | 73 |
| 4-Me-C₆H₄-B(OH)₂ | 4-Me-C₆H₄-CH(CF3)-BPin | 80 |

[a] Yields based on ¹H NMR analysis of the crude reaction mixture.
[b] Isolated yield.

Scheme 4C

F$_3$C-CH$_2$-NH$_3$Cl (2 equiv) → [NaNO$_2$, 1 h, 0 °C, Solvent/H$_2$O (10:1)] → [F$_3$C-CH=N$_2$] → 1. R—B(OH)$_2$ (1 equiv), [Si] (1.1 equiv), rt or 40 °C overnight; 2. KHF$_2$ (3 equiv) → R-CH(CF$_3$)-BF$_3$K

| substrate | product | | solvent | [Si] | isolated yield (%) |
|---|---|---|---|---|---|
| PhCH$_2$CH$_2$-BF$_3$K | PhCH$_2$CH$_2$-CH(CF$_3$)-BF$_3$K | 2a | CH$_2$Cl$_2$ | TMSCl | 71 |
| cyclopropyl-BF$_3$K | cyclopropyl-CH(CF$_3$)-BF$_3$K | 2b | toluene | TMSCl | 80 |
| cyclobutyl-BF$_3$K | cyclobutyl-CH(CF$_3$)-BF$_3$K | 2c | toluene | TMSCl | 78 |
| Ph(CH$_2$)$_3$CH=CH-BF$_3$K | Ph(CH$_2$)$_3$CH=CH-CH(CF$_3$)-BF$_3$K | 2d | CH$_2$Cl$_2$ | p-tolylSiCl$_3$ | 78 |
| PhC≡C-BF$_3$K | PhC≡C-CH(CF$_3$)-BF$_3$K | 2e | CH$_2$Cl$_2$ | TMSCl | 92 |
| 4-MeO-C$_6$H$_4$-BF$_3$K | 4-MeO-C$_6$H$_4$-CH(CF$_3$)-BF$_3$K | 2f | CH$_2$Cl$_2$ | p-tolylSiCl$_3$ | 71(67)[a] |
| 4-F-C$_6$H$_4$-BF$_3$K | 4-F-C$_6$H$_4$-CH(CF$_3$)-BF$_3$K | 2g | CH$_2$Cl$_2$ | TMSCl | 72 |
| 4-F$_3$C-C$_6$H$_4$-BF$_3$K | 4-F$_3$C-C$_6$H$_4$-CH(CF$_3$)-BF$_3$K | 2h | toluene | p-tolylSiCl$_3$ | 83 |
| 3-NC-C$_6$H$_4$-BF$_3$K | 3-NC-C$_6$H$_4$-CH(CF$_3$)-BF$_3$K | 2i | CH$_2$Cl$_2$ | TMSCl | 70 |

-continued

Scheme 4C

Reaction scheme: F$_3$C-CH$_2$-NH$_3$Cl (2 equiv) + NaNO$_2$, 1 h, 0° C., Solvent/H$_2$O (10:1) → [F$_3$C-CH=N$_2$] → 1. R—B(OH)$_2$ (1 equiv), [Si] (1.1 equiv), rt or 40° C. overnight; 2. KHF$_2$ (3 equiv) → R-CH(CF$_3$)-BF$_3$K

| substrate | product | | solvent | [Si] | isolated yield (%) |
|---|---|---|---|---|---|
| 3-Cl-C$_6$H$_4$-BF$_3$K | 3-Cl-C$_6$H$_4$-CH(CF$_3$)-BF$_3$K | 2j | CH$_2$Cl$_2$ | p-tolylSiCl$_3$ | 71 |
| 4-vinyl-C$_6$H$_4$-BF$_3$K | 4-vinyl-C$_6$H$_4$-CH(CF$_3$)-BF$_3$K | 2k | CH$_2$Cl$_2$ | TMSCl | 89 |
| 4-biphenyl-BF$_3$K | 4-biphenyl-CH(CF$_3$)-BF$_3$K | 2l | CH$_2$Cl$_2$ | p-tolylSiCl$_3$ | 65 |
| 2-naphthyl-BF$_3$K | 2-naphthyl-CH(CF$_3$)-BF$_3$K | 2m | CH$_2$Cl$_2$ | TMSCl | 88 |
| 1-Me-indol-5-yl-BF$_3$K | 1-Me-indol-5-yl-CH(CF$_3$)-BF$_3$K | 2n | CH$_2$Cl$_2$ | TMSCl | 90 |
| 3-thienyl-BF$_3$K | 3-thienyl-CH(CF$_3$)-BF$_3$K | 2o | CH$_2$Cl$_2$ | TMSCl | 72 |
| 2-furyl-BF$_3$K | 2-furyl-CH(CF$_3$)-BF$_3$K | 2p | toluene | TMSCl | 86 |

[a] Reaction performed on 10 mmol scale.

To demonstrate the value of the α-trifluoromethylated organoborons in synthesis, studies for the functionalization of the carbon-boron bond were performed. Reactions were carried out in situ on the α-trifluoromethylated, tricoordinate organoboron species. For example, oxidation was performed by quenching the crude reaction mixture with pinacol, followed by treatment with NaOH/H$_2$O$_2$ (Scheme 5, eq 2).

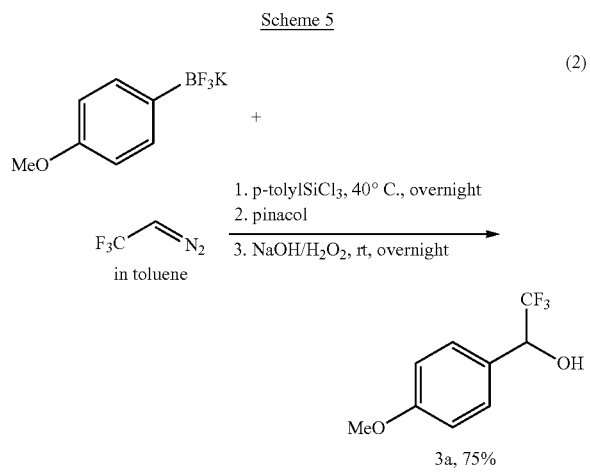

Adding N-bromosuccinimide (NBS) or N-chlorosuccinimide (NCS) in acetonitrile in situ to α-trifluoromethylated dihaloborane led to the corresponding bromide or chloride in moderate yields without any extensive optimization. When p-methoxyphenyltrifluoroborate was used, the desired trifluoromethylated benzyl bromide was isolated (Scheme 6, 3b). However, with an alkenyltrifluoroborate, the geminal trifluoromethylated bromides and chlorides were not obtained. Rearrangement occurred to provide the allylic bromide and chloride in a regio- and stereodefined manner.

Such an observation provides for still another set of embodiments, in which the product may be more generally described in terms of:

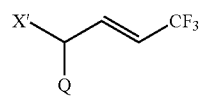

where X' is optionally substituted C$_{1-20}$alkyl; optionally substituted C$_{1-20}$heteroalkyl; optionally substituted C$_{1-20}$alkenyl; optionally substituted C$_{1-20}$alkynyl; optionally substituted cycloalkyl, optionally substituted heterocycloalkyl, optionally substituted aryl, or optionally substituted heteroaryl and Q is halogen, preferably Br, Cl, or F. These may be prepared by syntheses analogous to those described in Scheme 6 and associated text. Subsequent synthetic steps may also be used to prepare compounds where the halogen Q is transformed into hydrogen, optionally protected —OH, amine, optionally substituted aryl, or optionally substituted heteroaryl, using conventional transformational methods known to those skilled in the art—e.g., protodeboronation, oxidation, amination, halogenation, halogenation-cross-coupling, addition of aldehydes, or the Minisci reaction.

Protodeboronation of the crude α-trifluoro-methylated pinacol boronate can be effected under Aggarwal's conditions (Scheme 7, eq 3). (Nave, S.; Sonawane, R. P.; Elford, T. G.; Aggarwal, V. K. *J. Am. Chem. Soc.* 2010, 132, 17096-17098). This transformation provides a method of installing a trifluoroethyl group on an aromatic unit without employing any metal.

Scheme 7

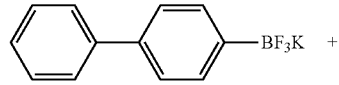

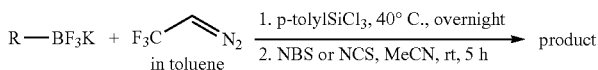

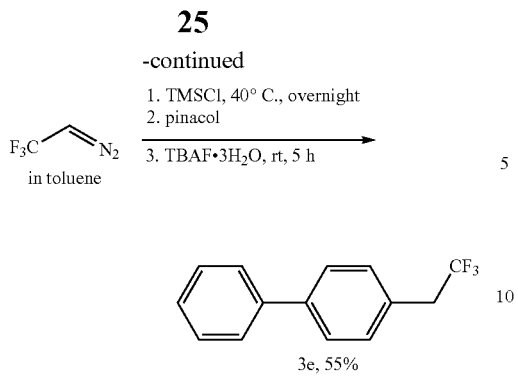

3e, 55%

Synthesis of substituted 1,1-difluoro-1,3-butadienes can be achieved by heating the intermediate dihaloborane species generated upon reaction of CF$_3$CHN$_2$ with an alkenyltrifluoroborate (Scheme 8, eq 4).

Scheme 8

(4)

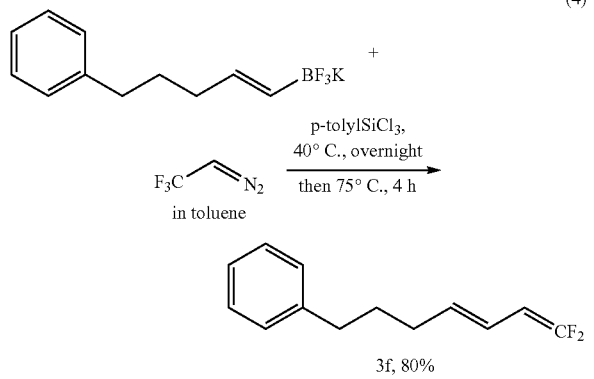

3f, 80%

Reaction of α-trifluoromethylated organoborons with a second diazo compound was performed. When ethyl diazoacetate was added in situ to the α-trifluoromethylated dihaloborane generated from the corresponding organotrifluoroborate, the "double diazo" insertion product was obtained in an overall (unoptimized) yield of 43%. It is important to note that this approach represents a complementary but more economical and expeditious method to access the same class of molecules that are obtained by the addition of the Ruppert-Prakash reagent to α,β-unsaturated esters (Scheme 9, eq 5), with the potential for providing access to greater structural diversity as well.

Scheme 9

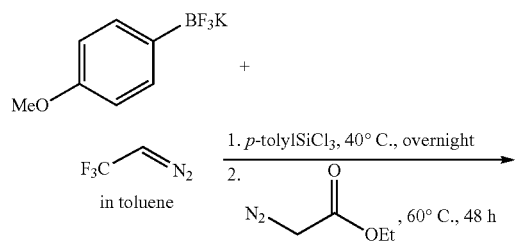

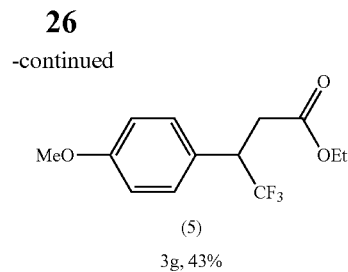

(5)

3g, 43%

Heteroaryl-boronic acids can be reacted with trifluoromethyl-diazomethane to produce heteroaryl-α-trifluoromethyl-containing compounds. See, e.g., Scheme 10.

Scheme 10

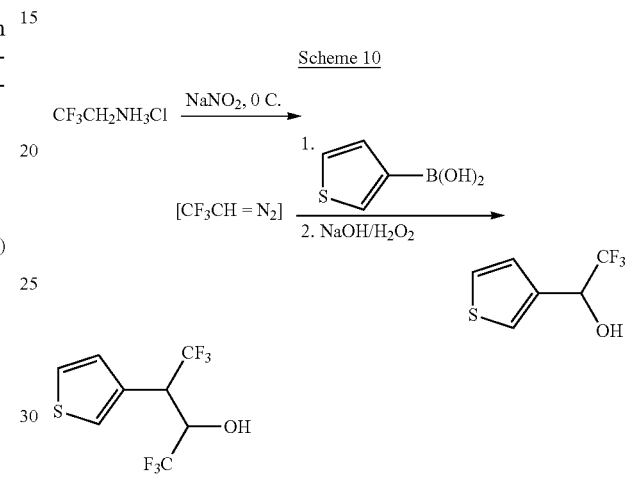

Heterocycloalkyl-containing compounds will also be produced according to the invention. See, e.g., Scheme 11.

Scheme 11

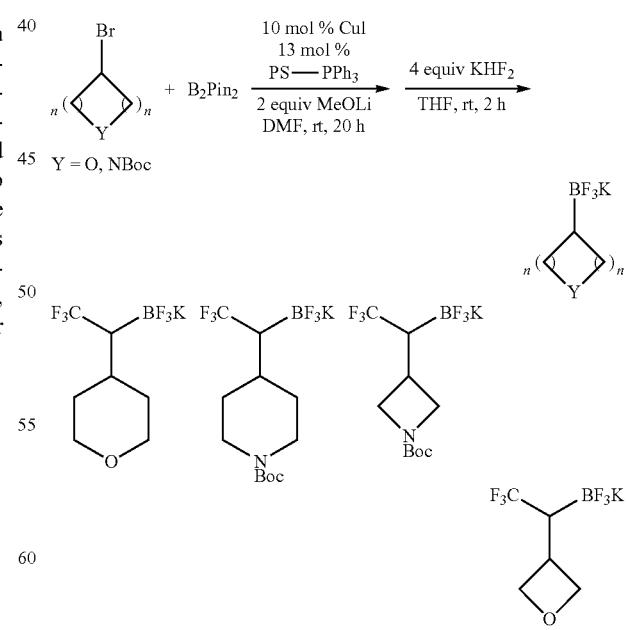

Chiral organotrifluoroborates, including those that are enantiomerically enriched (*) are also within the scope of the invention. See below Scheme 12.

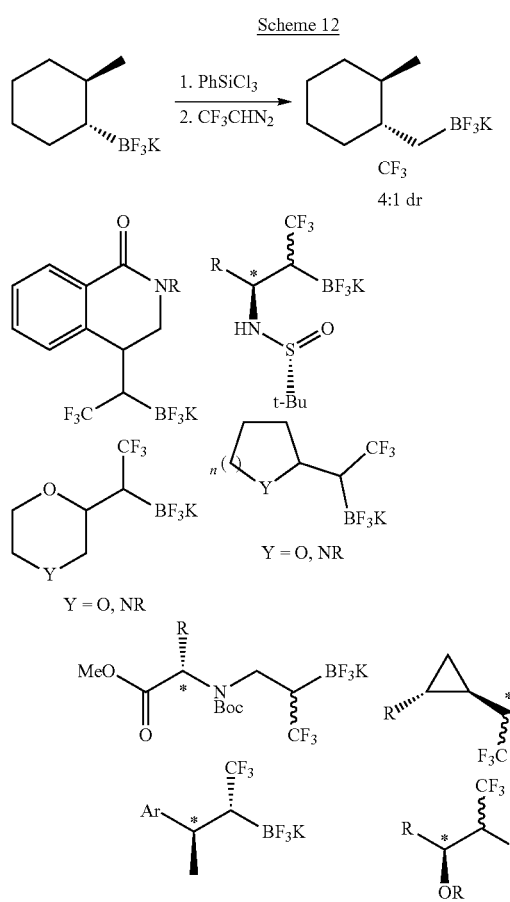

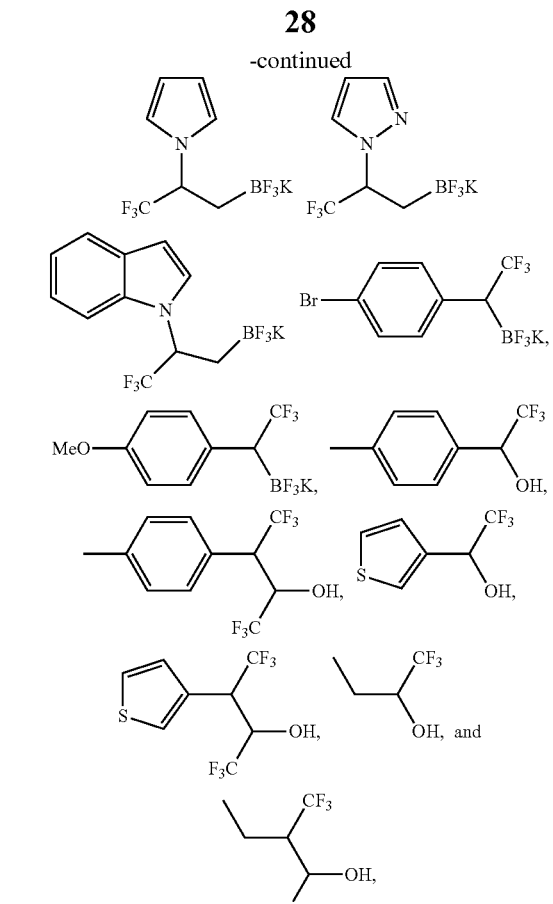

Trifluoromethylated allyltrifluoroborates will also accessible using the methods of the invention. See e.g., Scheme 13.

It should be appreciated that each and every compound described within this disclosure is a considered separate embodiment, within the scope of the present invention.

Scheme 13

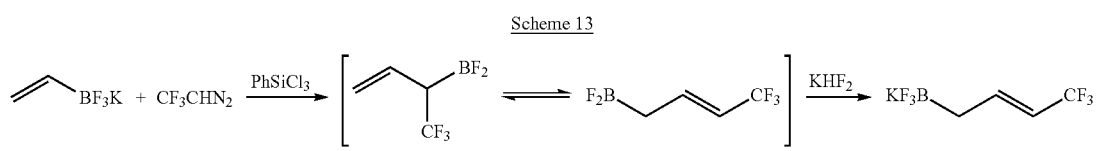

Examples for compounds that can be prepared according to the methods described herein include any of those described herein, but also including:

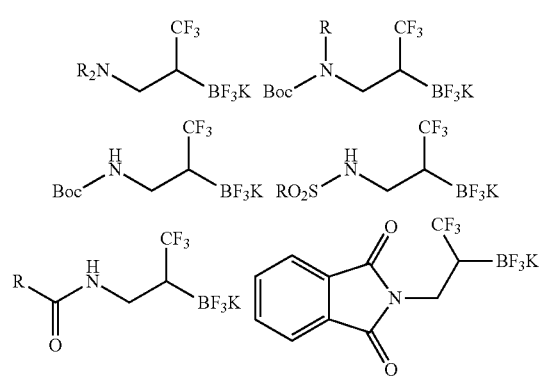

The following listing of Embodiments is intended to complement, rather than displace or supersede, the previous descriptions.

One embodiment of the invention is a compound of formula I-A:

I-A wherein n is an integer from 1 to 15;

X is optionally substituted $C_{1-20}$alkyl; optionally substituted cycloalkyl, optionally substituted heterocycloalkyl, optionally substituted aryl, or optionally substituted heteroaryl; and Y is H, —B-pinacol; —B(OR)$_2$; —BF$_3$K; OH; BZ$_2$; —NR$_2$, wherein Z is each R is independently H or C$_{1-6}$alkyl; optionally substituted C$_{1-20}$alkyl; optionally substituted aryl; optionally substituted heteroaryl; or halogen.

In some embodiments of the compounds of formula I-A, n is 1 to 5.

In some embodiments of the compounds of formula I-A, n is 6 to 10.

In some embodiments of the compounds of formula I-A, n is 11 to 15.

In some embodiments of the compounds of formula I-A, n is 1 or 2.

In some embodiments of the compounds of formula I-A, n is 1.

In some embodiments of the compounds of formula I-A, X is optionally substituted aryl. In those embodiments wherein X is optionally substituted aryl, the aryl is substituted with 1, 2, or 3 C$_{1-6}$alkyl; —OC$_{1-6}$alkyl; halogen; —CF$_3$; —SO$_2$N(R$^1$)$_2$, wherein R$^1$ is H or C$_{1-6}$alkyl; nitro, —OH, or —CN.

In some embodiments of the compounds of formula I-A, X is optionally substituted heteroaryl. In those embodiments wherein X is optionally substituted heteroaryl, the heteroaryl is furanyl, imidazolyl, pyrrolidinyl, pyrimidinyl, tetrazolyl, thienyl, pyridyl, pyrrolyl, N-methylpyrrolyl, quinolinyl, or isoquinolinyl. In those embodiments wherein the heteroaryl is substituted, the heteroaryl is substituted with 1, 2, or 3 C$_{1-6}$alkyl; —OC$_{1-6}$alkyl; halogen; —CF$_3$; —SO$_2$N(R$^1$)$_2$, wherein R$^1$ is H or C$_{1-6}$alkyl; nitro; —OH, or —CN.

In some embodiments of the compounds of formula I-A, Y is B-pinacol; —B(OR)$_2$, —B(OH)$_2$, —BF$_3$K, BX$_2$, or —OH.

In some embodiments of the compounds of formula I-A, when n is 1, Y is B-pinacol; —B(OR)2, —B(OH)2; —BF3K; or BZ2.

In some embodiments of the compounds of formula I-A, Y is —OH.

Preferred compounds of formula I-A the present invention include:

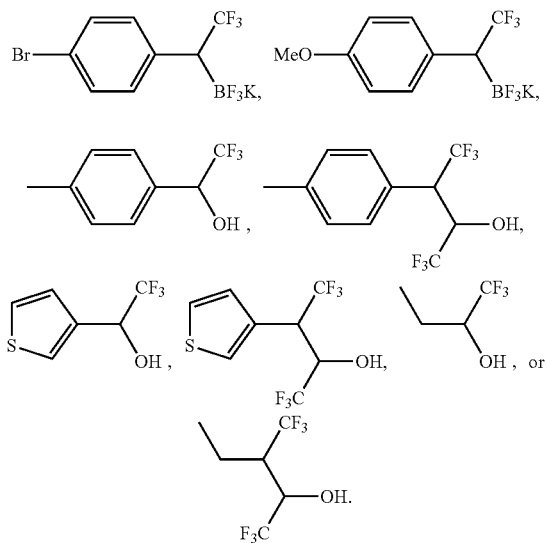

Within the scope of the invention are compounds of formula I-A that are isolated compounds.

Also within the scope of the invention are methods of generating a compound having an aryl- or heteroaryl-α-trifluoromethyl group comprising:

reacting an aryl-B(OH)$_2$ or heteroaryl-B(OH)$_2$ with CF$_3$—CH=N$_2$ to form a trifluoromethyl intermediate; and reacting the trifluoromethyl intermediate with KHF$_2$, pinacol, or an oxidizing reagent, or water to form the compound having an aryl- or heteroaryl-α-trifluoromethyl group;

wherein the aryl and heteroaryl are optionally substituted.

Oligomer or polymer produced according to the methods of the invention are also within the scope of the invention.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric. The term "RT" refers to ambient room temperature, this being in the case of these experiment about 20-23° C.

In general, the reactions are conducted under inert atmospheres, such as under nitrogen or argon, and relatively mild temperatures (i.e., in a range of from about 0° C. to about 60° C., preferably at temperatures ranging from ambient room temperature to about 40° C.) for times in a range of from about 2 to about 40 hours, preferably from about 4 to about 25 hours.

I. Preparation of Stock Solution of Trifluorodiazoethane

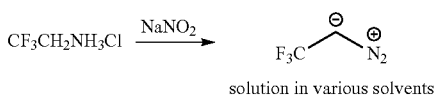

solution in various solvents

Trifluoroethylamine hydrochloride (13.55 g, 100 mmol) and sodium nitrite (7.59 g, 110 mmol) were added to a 500 mL round bottom flask equipped with a stir bar, and the flask was sealed with a septum and purged with argon three times. Degassed toluene (200 mL) was added, and the reaction mixture was cooled to 0° C. upon stirring under Ar for 30 min. Degassed H$_2$O (20 mL) was added under Ar. The solution was stirred for 2 h at 0° C., then for an additional 30 min at 10° C. under Ar. The aqueous layer was frozen in the freezer overnight (~–18° C.). The organic layer was then transferred to a flame-dried round bottom flask and dried (K$_2$CO$_3$, 10 g) for 1 h. The concentration of the yellow solution of 2,2,2-trifluorodiazoethane was analyzed by $^{19}$F NMR using trifluorotoluene as an internal standard. The solution of 2,2,2-trifluoroethyldiazomethane was obtained in yields ranging between 85-95%, in a concentration of 0.43-0.47 M.

Stock solutions of trifluorodiazoethane ranging between 0.1 M and 0.5 M in toluene, trifluorotoluene, dichloromethane, 1,2-dichloroethane, chlorobenzene, and heptane were prepared via a similar procedure.

II. Synthesis of Trifluoromethylated Boronate Esters

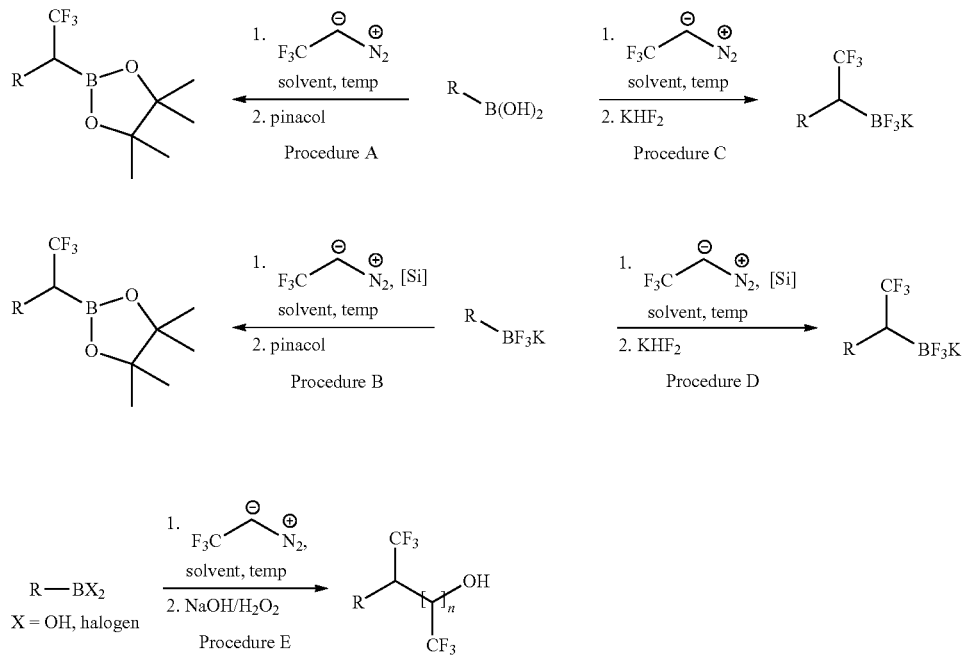

General Procedure for the Synthesis of Trifluoromethylated Potassium Organotrifluoroborates Potassium organotrifluoroborate (1 mmol) was added into a 20 mL Biotage microwave vial equipped with a stir bar. The vial was sealed and purged with argon three times. A solution of $CF_3CHN_2$ in $CH_2Cl_2$ (~0.5 M, 4 mL) or toluene (~0.5 M, 4 mL) was added under Ar. Then freshly distilled $Me_3SiCl$ (120 mg, 1.1 mmol) or p-tolylSiCl$_3$ (248 mg, 1.1 mmol) was added, and the reaction was stirred at ambient room temperature ("RT," or about 20-23° C.) in $CH_2Cl_2$ or about 40° C. in toluene overnight. The reaction was cooled to 0° C., then a saturated solution of $KHF_2$ (1 mL, 4.5 M) was added dropwise under Ar. Acetone (3 mL) was added to increase the solubility and improve the stirring of the reaction. The reaction was allowed to warm to RT and stirred for an additional 30 min under Ar. The solvent was evaporated from the crude reaction mixture, and the product was extracted into dry acetone to eliminate the inorganic salts. The acetone was evaporated and the desired product was recrystallized from the crude mixture.

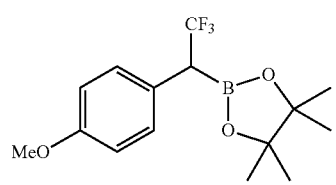 [SMILES: COc1ccc(C(B2OC(C)(C)C(C)(C)O2)C(F)(F)F)cc1]

[(4-Methoxyphenyl)-2,2,2-trifluoroethyl)] pinacol boronate

Procedure A (from Boronic Acid):

4-Methoxyphenylboronic acid (151 mg, 1 mmol) was added to a 20 mL Biotage microwave vial equipped with a stir bar. The vial was sealed and purged with argon three times. The solution of 2,2,2-trifluorodiazoethane in $ClCH_2CH_2Cl$ (0.25 M, 8 mL) was added under Ar, and the reaction was stirred at room temperature overnight. The reaction was quenched with pinacol (112 mg, 0.95 mmol) in $CH_2Cl_2$ (2 mL) for 1 h at RT under Ar. The crude was rapidly passed through a short plug of Celite, then concentrated under vacuum to provide the compound as a light yellow oil (275 mg, 87%) of ~80% purity. IR (neat) 1514, 1348, 1247, 1136, 1083, 969, 851, 736 cm-1; 1H NMR (500 MHz, CDCl3) δ 7.27 (d, J=8.6 Hz, 2H), 6.88 (d, J=8.7 Hz, 2H), 3.79 (s, 3H), 3.16 (q, J=11.5 Hz, 1H), 1.29 (s, 6H), 1.25 (s, 6H); 13C NMR (126 MHz, CDCl3) δ 159.3, 131.5, 127.0 (q, J=277.2 Hz), 124.1 (q, J=2.9 Hz), 114.2, 84.7, 55.3, 37.8, 24.6 (d, J=15.1 Hz); 19F NMR (282 MHz, CDCl3) δ −63.18 (d, J=11.3 Hz); 11B NMR (128 MHz, CDCl3) δ 30.46; HRMS (ESI-TOF) m/z calcd. for $C_{15}H_{20}BO_3F_3$ 316.1458. found 316.1460.

The following tabulated products were prepared using Procedure A, except where toluene or 1,2-dichloroethane (DCE) was used as the solvent and boroxine was used as the boron-containing starting material.

TABLE 1
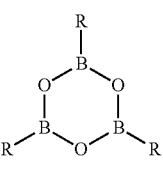
| R | Equiv of F₃C−CH=N₂ | Time (hr) | T (° C.) | d.r.[a] | Yield (%)[b] |
|---|---|---|---|---|---|
| 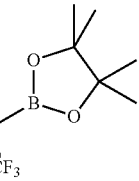 | 4 | 21.5 | RT | 50:1 | 62 |
| 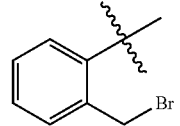 [SMILES: *c1ccccc1CBr] | 4 | 14 | RT | 20:1 | 59 |
| 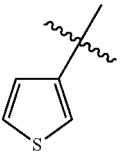 [SMILES: *c1ccsc1] | 8 | 15 | RT | 12.5:1 | 51 |
| 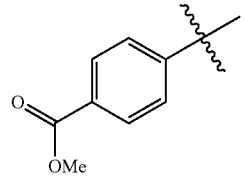 [SMILES: *c1ccc(C(=O)OC)cc1] | 4 | 2.8 | RT | 11.1:1 | 63 |
| 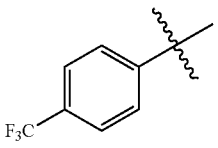 [SMILES: *c1ccc(C(F)(F)F)cc1] | 5 | 20.3 | RT | 20:1 | 60 |
| 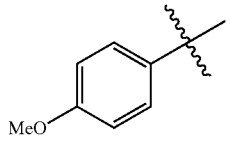 [SMILES: *c1ccc(OC)cc1] | 10 (1M, DCE) | 18.5 | 40 | 5.6:1 | 65 |
| 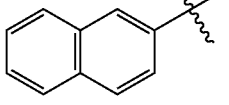 | 4 | 6 | RT | 12:1 | 58 |

TABLE 1-continued
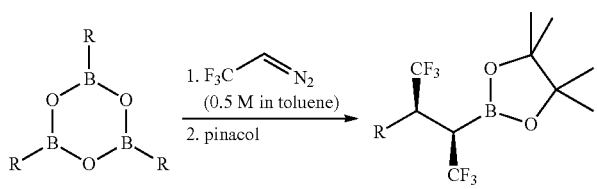
| R | Equiv of $F_3C\!\!-\!\!\overset{}{=}\!\!N_2$ | Time (hr) | T (° C.) | d.r.[a] | Yield (%)[b] |
|---|---|---|---|---|---|
| 4-vinylphenyl | 4 | 14 | RT | 10:1 | 48 |
| (E)-styryl | 4 | 16 | RT | 11.1:1 | 42 |
| 4-biphenyl | 6 (1M) | 16 | 37 | 14.3:1 | 69 |
| 3-chlorophenyl | 4 | 6.5 | RT | 11.1:1 | 46 |
| 3-methoxyphenyl | 4 | 14 | RT | 10:1 | 56 |
| 3-fluorophenyl | 4 | 4.5 | RT | 11.5:1 | 71 |
[a]d.r. is diastereomeric ratio, determined before isolation of the product
[b]% Yield is the isolated yield of the single diasteriomer TABLE 2
| R | Equiv of F₃C⌒N₂ | [F₃C⌒N₂] | Time (hr) | Yield (%)[a] |
|---|---|---|---|---|
| 2-naphthyl | 5 | 1M, DCE | 16 | A, 70 |
| 4-biphenyl | 6 | 1M, toluene | 16 | A, 72 |
| 1-methyl-5-indolyl | 6 | 0.5M, toluene | 12.5 | B. 43 |
| 4-methoxyphenyl | 4 | 0.5M, toluene | 13.25 | A, 65 |
| 2-(bromomethyl)phenyl | 5 | 0.5M, toluene | 14.5 | A, 67 |
| (E)-styryl | 5 | 0.5M, toluene | 12 | A, 55 |
[a]Designators A and B refer to the major product of the reaction and their respective yield
TABLE 3
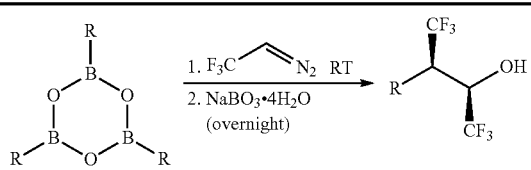

TABLE 3-continued
| R | Equiv of F₃C-CH=N₂ | [F₃C-CH=N₂] | Time (hr)ᵃ | Yield (%) |
|---|---|---|---|---|
| 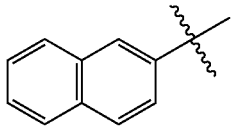 [SMILES: *c1ccc2ccccc2c1] | 10 | 1M, DCEᵇ | 14 | 64 |
| 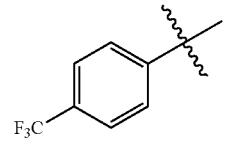 [SMILES: *c1ccc(C(F)(F)F)cc1] | 4 | 0.5M, toluene | 3 | 60 |
| 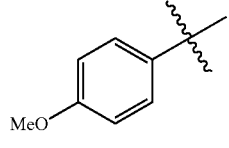 | 4 | 0.5M, toluene | 20 | 63 |
| 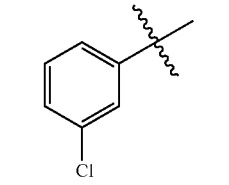 [SMILES: *c1cccc(Cl)c1] | 4 | 0.5M, toluene | 7 | 51 |
| R | F₃C-CH=N₂ | Time (hr) | Temp (° C.) | Yield (%) |
|---|---|---|---|---|
| 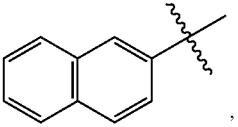, A | 10 (1M, DCE) | 18.5 | 40 | 65 |
| 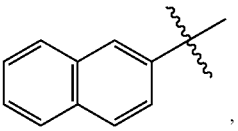 [SMILES: *c1ccc2ccccc2c1], B | 5 | 16 | 60 | A, 70 |
| 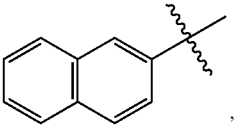, C | 10 | 14 | RT | 64 |
| 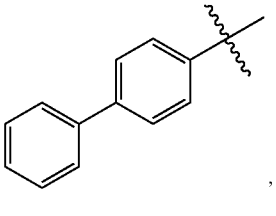 [SMILES: *c1ccc(-c2ccccc2)cc1], A | 6 | 16 | 37 | 69 |

TABLE 3-continued

| Structure | | | | |
|---|---|---|---|---|
| 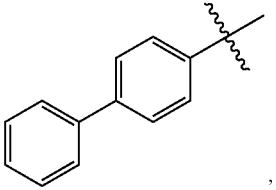 [SMILES: *c1ccc(-c2ccccc2)cc1] B | 6 | 16 | 60 | A, 72 |
| 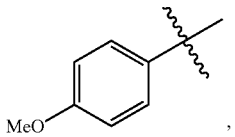 A | 5 | 20 | RT | 60 |
| 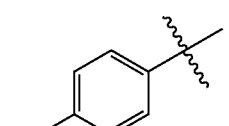 B | 4 | 13 | 60 | A, 65 |
| 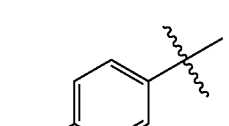 C | 4 | 20 | RT | 63 |

[a]Times refer to step 1; both steps 1 and 2 conducted at ambient room temperature
[b]DCE = 1,2-dichloroethane Procedure B (from Potassium Organotrifluoroborate):

Potassium 4-methoxyphenyl-trifluoroborate (151 mg, 1 mmol) was added to a 20 mL Biotage microwave vial equipped with a stir bar. The vial was sealed and purged with argon three times. The solution of 2,2,2-trifluorodiazoethane in $CH_2Cl_2$ (0.5 M, 4 mL) was added under Ar, then freshly distilled $Me_3SiCl$ (109 mg, 1 mmol) was added, and the reaction was stirred at RT overnight. The reaction was quenched with pinacol (112 mg, 0.95 mmol) in $CH_2Cl_2$ (2 mL) for 1 h at RT under Ar. The crude mixture was rapidly passed through a short plug of Celite, then concentrated under vacuum to provide the compound as a light yellow oil (294 mg, 93%) of ~90% purity. The crude product was purified on silica gel column chromatography to provide the desired pure product as a colorless oil (136 mg, 43%).

Procedure B-1:

Potassium organotrifluoroborate (1 mmol) was added to a 20 mL Biotage microwave vial equipped with a stir bar. The vial was sealed and purged with argon three times. The solution of 2,2,2-trifluorodiazoethane in $CH_2Cl_2$ (~0.5 M, 4 mL) or toluene (~0.5 M, 4 mL) was added under Ar, then freshly distilled $Me_3SiCl$ (120 mg, 1.1 mmol) or p-tolyl-$SiCl_3$ (248 mg, 1.1 mmol) was added, and the reaction was stirred at RT (in $CH_2Cl_2$) or 40° C. (in toluene) overnight. The pressure was vented under Ar pressure. The reaction was cooled to 0° C., then a saturated solution of $KHF_2$ (1 mL, 4.5 M in $H_2O$) was added dropwise under Ar. Acetone (3 mL) was added to increase the solubility and improve the stirring of the reaction. The reaction was allowed to warm to RT and stirred for an additional 30 min under argon. The solvent was evaporated from the crude reaction mixture, and the product was extracted into dry acetone to eliminate the inorganic salts. The acetone was evaporated and the desired product was recrystallized from the crude mixture Heptane, toluene, trifluorotoluene, dichloroethane or chlorobenzene can be used as a solvent instead of dichloromethane. The reaction was performed at temperatures of ambient room temperature (RT, ca. 20-23° C.), 40, 50 and 60° C. Silicon tetrachloride, $MeSiCl_3$, c-$C_5H_9$—$SiCl_3$, $PhSiCl_3$ or 4-Me-$C_6H_4$—$SiCl_3$ were used as a fluorophile instead of TMSCl to provide the desired compound in yields ranging between 10% to 85% with purities ranging between 80% to 95%.

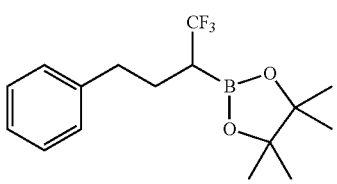 [SMILES: CC1(C)OB(C(CCc2ccccc2)C(F)(F)F)OC1(C)C]

[(2-Phenylethyl)-2,2,2-trifluoroethyl)] pinacol boronate

Using procedure B, starting from potassium 2-phenylethyltrifluoroborate (212 mg, 1 mmol) the compound was obtained as a colorless oil (289 mg, 92%), ~80% purity without purification on silica gel column chromatography. After purification on silica gel column chromatography, the compound was obtained as a colorless oil (169 mg, 54%), >95% purity. mp 173-176° C.; IR (neat) 1328, 1252, 1134, 1096, 1057, 996, 962, 639 cm$^{-1}$; $^1$H NMR (500 MHz, acetone-d6) δ 7.28-7.17 (m, 4H), 7.16-7.08 (m, 1H), 2.78-2.67 (m, 2H), 1.90-1.83 (m, 1H), 1.75-1.73 (m, 1H), 1.13 (s, 1H); $^{13}$C NMR (126 MHz, acetone-d6) δ 143.9, 132.2 (q, J=278.1 Hz), 128.5, 128.2, 125.4, 35.7, 34.3, 27.9; $^{19}$F NMR (471 MHz, acetone-d6) δ −61.56, −142.85 (q, J=51.8 Hz); $^{11}$B NMR (128 MHz, acetone-d6) δ 3.22 (q, J=55.0 Hz); HRMS (ESI-TOF) m/z calcd. for $C_{10}H_{10}BF_6^-$[M−K]$^-$ 255.0780. found 255.07803.

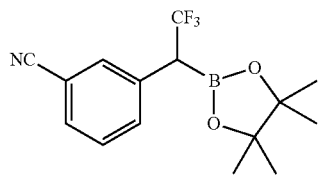 [SMILES: CC1(C)OB(C(c2cccc(C#N)c2)C(F)(F)F)OC1(C)C]

[(3-Cyanophenyl)-2,2,2-trifluoroethyl)] pinacol boronate

Using procedure B, starting from potassium 3-cyanophenyltrifluoroborate (209 mg, 1 mmol) the compound was obtained as a colorless oil (295 mg, 95%), ~90% purity, without purification on silica gel column chromatography.

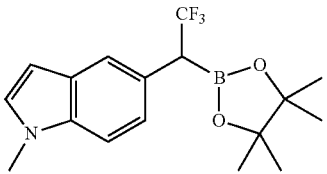 [SMILES: Cn1ccc2cc(C(B3OC(C)(C)C(C)(C)O3)C(F)(F)F)ccc21]

[(5-N-Methylindolyl)-2,2,2-trifluoroethyl)] pinacol boronate

Using procedure B, starting from potassium 5-N-methylindolyltrifluoroborate (237 mg, 1 mmol) the compound was obtained as an orange waxy solid after purification by column chromatography (115 mg, 34%), >95% purity.

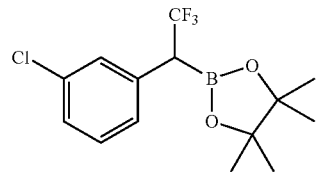 [SMILES: CC1(C)OB(C(c2cccc(Cl)c2)C(F)(F)F)OC1(C)C]

[(3-Chlorophenyl)-2,2,2-trifluoroethyl)] pinacol boronate

Using procedure B, starting from potassium 3-chlorophenyltrifluoroborate (218 mg, 1 mmol) the compound was obtained as a colorless oil (272 mg, 85%), ~80% purity, without purification on silica gel chromatography.

III. Synthesis of Trifluoromethylated Potassium Organotrifluoroborates

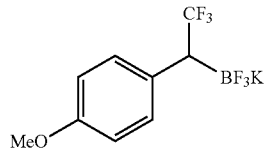

Procedure C (from Boronic Acid):

4-Methoxyphenylboronic acid (214 mg, 1 mmol) was added into a 20 mL Biotage microwave vial equipped with a stir bar. The vial was sealed and purged with argon three times. The solution of 2,2,2-trifluorodiazoethane in ClCH$_2$CH$_2$Cl (0.25 M, 8 mL) was added under Ar, and the reaction was stirred at RT overnight. The reaction was cooled to 0° C., then a saturated solution of KHF$_2$ (1 mL, 4.5 M) was added dropwise. Acetone (4 mL) was then added to increase the solubility and improve the stirring of the reaction. The reaction was allowed to warm to RT and stirred for an additional 30 min under Ar. The crude mixture was evaporated, and the product was extracted in dry acetone to eliminate the inorganic salts. The acetone was evaporated and the product was obtained as a white solid (278 mg, 94%), ~80% purity. The product of 80% purity was recrystallized in acetone/hexane to provide the pure product as a white solid (177 mg, 60%).

Procedure D (from Potassium Organotrifluoroborate):

Potassium 4-methoxyphenyl-trifluoroborate (214 mg, 1 mmol) was added into a 20 mL Biotage microwave vial equipped with a stir bar. The vial was sealed and purged with argon three times. The solution of 2,2,2-trifluorodiazoethane in CH$_2$Cl$_2$ (0.5 M, 4 mL) was added under Ar, then freshly distilled Me$_3$SiCl (109 mg, 1 mmol) was added, and the reaction was stirred at RT overnight. The reaction was cooled to 0° C., then a saturated solution of KHF$_2$ (1 mL, 4.5 M) was added dropwise. Acetone (3 mL) was added to increase the solubility and improve the stirring of the reaction. The reaction was allowed to warm to RT and stirred for an additional 30 min under Ar. The solvent was evaporated from the crude reaction mixture, and the product was extracted into dry acetone to eliminate the inorganic salts. The acetone was evaporated and the product was obtained as a white solid (281 mg, 95%), ~90% purity. The product of 90% purity was recrystallized in acetone/hexane to provide the pure product as a white solid (192 mg, 65%).

Heptane, toluene, trifluorotoluene, dichloroethane or chlorobenzene can be used as a solvent instead of dichloromethane. The reaction was performed at temperatures of RT, 40, 50 and 60° C. Silicon tetrachloride, MeSiCl$_3$, c-C$_5$H$_9$—SiCl$_3$, PhSiCl$_3$ or 4-Me-C$_6$H$_4$—SiCl$_3$ were used as a fluorophile instead of TMSCl to provide the desired compound in yields ranging between 20% to 85% with purities ranging between 80% to 95%.

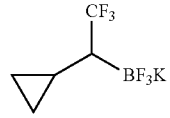

(2b)

Potassium (1-Cyclopropyl-2,2,2-trifluoroethyl)trifluoroborate

Following the general procedure, starting from potassium 1-cyclopropyltrifluoroborate (148 mg, 1 mmol), using toluene (~1 M CF$_3$CHN$_2$, 2 mL) and TMS-Cl at RT, the desired product was obtained as a white solid (184 mg, 80%) after the unreacted 1-cyclopropyltrifluoroborate was removed by recrystallization in acetone/Et$_2$O, and the filtrate was evaporated; mp 224-227° C.; IR (neat) 1317, 1254, 1229, 1163, 1120, 1054, 997, 966, 944, 848, 788, 750, 690, 620 cm$^{-1}$; $^1$H NMR (500 MHz, acetone-d6) δ 0.78-0.76 (m, 1H), 0.40-0.28 (m, 3H), 0.14-0.09 (m, 2H); $^{13}$C NMR (126 MHz, acetone-d6) δ 132.0 (q, J=278.5 Hz), 39.8, 7.5 (d, J=3.8 Hz), 4.31, 3.33; $^{19}$F NMR (471 MHz, acetone-d6) δ −62.05, −142.36 (q, J=51.8 Hz); $^{11}$B NMR (128 MHz, acetone-d6) δ 3.52 (q, J=55.1 Hz); HRMS (ESI-TOF) m/z calcd. for C$_5$H$_6$BF$_6^-$[M−K]$^-$ 191.0467. found 191.0494.

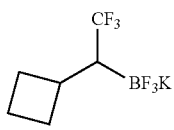

Potassium (1-cyclobutyl-2,2,2-trifluoroethyl)trifluoroborate

Following procedure D, starting from potassium 1-cyclobutyltrifluoroborate (324 mg, 2 mmol), the desired product was obtained as a white solid (385 mg, 79%), >95% purity without recrystallization.

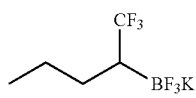

Potassium (1-butyl-2,2,2-trifluoroethyl)trifluoroborate

Following procedure C, starting from n-butylboronic acid (102 mg, 1 mmol), the desired product was obtained as a white solid (362 mg, 78%), ~80% purity without recrystallization.

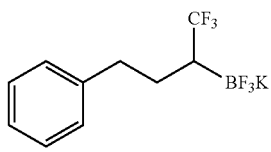

Potassium [(2-phenylethyl)-2,2,2-trifluoroethyl]trifluoroborate

Following procedure D, starting from potassium 2-phenylethyltrifluoroborate (212 mg, 1 mmol), the desired product was obtained as a white solid (262 mg, 89%), ~90% purity without recrystallization.

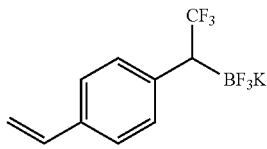

Potassium (4-vinylphenyl-2,2,2-trifluoroethyl)trifluoroborate

Following procedure D, starting from potassium 4-vinylphenyltrifluoroborate (525 mg, 2.5 mmol), the desired product was obtained as a white solid (562 mg, 77%), >95% purity, without recrystallization.

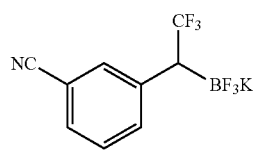

Potassium (3-cyanophenyl-2,2,2-trifluoroethyl)trifluoroborate

Following procedure C, starting from potassium 3-cyanophenyltrifluoroborate (209 mg, 1 mmol), the desired product was obtained as a white solid (162 mg, 56%), ~90% purity.

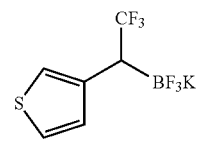

Potassium (3-thienyl-2,2,2-trifluoroethyl)trifluoroborate

Following procedure D, starting from potassium 3-thienyltrifluoroborate (190 mg, 1 mmol), the desired product was obtained as a white solid (122 mg, 45%), >95% purity.

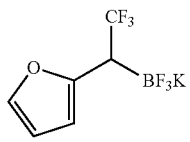

Potassium (2-furyl-2,2,2-trifluoroethyl)trifluoroborate

Following procedure D, starting from potassium 2-furyltrifluoroborate (173 mg, 1 mmol), the desired product was obtained as a white solid (117 mg, 46%), >95% purity.

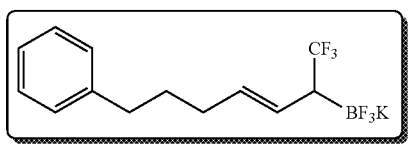

Potassium (E)-(1,1,1-Trifluoro-7-phenylhept-3-en-2-yl)trifluoroborate (2d)

Following the general procedure, starting from potassium (E)-(5-phenylpent-1-enyl)trifluoroborate (252 mg, 1 mmol), using $CH_2Cl_2$ and p-tolylSiCl$_3$, the desired product was obtained as a white solid (261 mg, 78%), after recrystallization in acetone/hexane/Et$_2$O; mp 118° C. (decomposes); IR (neat) 1249, 1166, 1071, 1041, 750, 699, 668 cm$^{-1}$; $^1$H NMR (500 MHz, acetone-d6) δ 7.30-7.17 (m, 4H), 7.13 (t, J=7.0 Hz, 1H), 5.50-5.45 (m, 1H), 5.37-5.26 (m, 1H), 2.66-2.57 (m, 2H), 2.02-1.98 (m, 2H), 1.90 (s, 1H), 1.69-1.60 (m, 2H); $^{13}$C NMR (126 MHz, acetone-d6) δ 142.9, 130.5 (q, J=276.4 Hz), 129.9, 128.6, 128.3, 127.6, 125.6, 41.1, 35.0, 32.2, 31.6; $^{19}$F NMR (471 MHz, acetone-d6) δ −61.70, −142.84 (q, J=50.2 Hz); $^{11}$B NMR (128 MHz, acetone-d6) δ 2.99 (q, J=49.9 Hz); HRMS (ESI-TOF) m/z calcd. for $C_{13}H_{14}BF_6^-$ [M−K]$^-$ 295.1093. found 295.1093.

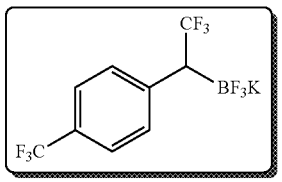

Potassium Trifluoro(1,1,1-trifluoro-4-phenylbut-Syn-2-yl)borate (2e)

Following the general procedure, starting from potassium trifluoro(phenylethynyl)borate (208 mg, 1 mmol), using $CH_2Cl_2$ and TMS-Cl, the desired product was obtained as an off-white solid (267 mg, 92%), after recrystallization in toluene/hexane; mp 127° C. (decomposes); IR (neat) 1339, 1250, 1153, 1097, 1021, 967, 859, 752, 688 cm$^{-1}$; $^1$H NMR (500 MHz, acetone-d6) δ 7.38-7.31 (m, 2H), 7.32-7.21 (m, 3H), 2.40 (s, 1H); $^{13}$C NMR (126 MHz, acetone-d6) δ 131.4, 128.7 (q, J=276.4 Hz), 128.3, 127.2, 125.2, 88.8, 80.3; $^{19}$F NMR (471 MHz, acetone-d6) δ −62.26, −142.57 (q, J=45.5 Hz); $^{11}$B NMR (128 MHz, acetone-d6) δ 2.43 (q, J=46.1 Hz); HRMS (ESI-TOF) m/z calcd. for $C_{10}H_6BF_6^-$ [M−K]$^-$ 251.0467. found 251.0463.

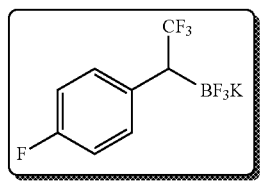

Potassium Trifluoro[2,2,2-trifluoro-1-(4-fluorophenyl)ethyl]borate (2g)

Following the general procedure, starting from potassium 4-fluorophenyltrifluoroborate (202 mg, 1 mmol), using $CH_2Cl_2$ and TMS-Cl, the desired product was obtained as a white solid (204 mg, 72%) after recrystallization in toluene/acetone; mp at 218° C. (decomposes); IR (neat) 1511, 1351, 1264, 1231, 1186, 1134, 1100, 1082, 1051, 1003, 960, 880, 830, 764, 618 cm$^{-1}$; $^1$H NMR (500 MHz, acetone-d6) δ 7.37-7.25 (m, 2H), 6.95-6.81 (m, 2H), 2.48 (s, 1H); $^{13}$C NMR (126 MHz, acetone-d6) δ 161.1 (d, J=240.4 Hz), 135.8, 131.6 (d, J=7.6 Hz), 131.7, 130.1 (q, J=277.7 Hz), 113.8 (d, J=21.4 Hz), 43.2; $^{19}$F NMR (471 MHz, acetone-d6) δ −60.58, −121.38 (d, J=5.2 Hz), −142.22 (q, J=50.2 Hz); $^{11}$B NMR (128 MHz, acetone-d6) δ 3.17 (q, J=51.8 Hz); HRMS (ESI-TOF) m/z calcd. for $C_8H_5BF_7^-$ [M−K]$^-$ 245.0373. found 245.0372.

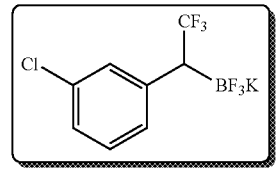

Potassium Trifluoro{2,2,2-trifluoro-1-[4-(trifluoromethyl)phenyl]ethyl}borate (2h)

Following the general procedure, starting from potassium 4-trifluoromethylphenyltrifluoroborate (252 mg, 1 mmol), using toluene and p-tolylSiCl$_3$, the desired product was obtained as a white solid (277 mg, 83%) after sonicating in hexane/toluene; mp 186-194° C.; IR (neat) 1327, 1247, 1114, 1070, 960, 829 cm$^{-1}$; $^1$H NMR (500 MHz, acetone-d6) δ 7.49 (s, 4H), 2.62 (s, 1H); $^{13}$C NMR (126 MHz, acetone-d6) δ 145.4, 131.1, 130.6 (q, J=277.7 Hz), 127.6 (q, J=31.5 Hz), 125.8 (q, J=270.6 Hz), 125.0 (q, J=3.8 Hz), 45.1; $^{19}$F NMR (471 MHz, acetone-d6) δ −59.88, −62.54, −142.35 (q, J=48.6 Hz); $^{11}$B NMR (128 MHz, acetone-d6) δ 2.90 (q, J=49.5 Hz); HRMS (ESI-TOF) m/z calcd. for $C_8H_5BF_9^-$ [M−K]$^-$ 295.0341. found 295.0341.

Potassium [1-(3-chlorophenyl)-2,2,2-trifluoroethyl]trifluoroborate (2j)

Following the general procedure, starting from potassium 3-chlorophenyltrifluoroborate (219 mg, 1 mmol), using $CH_2Cl_2$ and p-tolylSiCl$_3$, the desired product was obtained as a light brown solid (213 mg, 71%) after sonicating in Et$_2$O/hexane; mp>250° C.; IR (neat) 1348, 1249, 1188, 1148, 1089, 1056, 1000, 964, 908, 858, 764, 711, 700 cm$^{-1}$;

$^1$H NMR (500 MHz, acetone-d6) δ 7.38 (s, 1H), 7.22 (d, J=7.6 Hz, 1H), 7.16 (t, J=7.8 Hz, 1H), 7.10-7.08 (m, 1H), 2.49 (s, 1H); $^{13}$C NMR (126 MHz, acetone-d6) δ 142.6, 132.7, 130.0 (q, J=276.8 Hz), 129.8, 128.9, 128.7, 124.9, 44.4; $^{19}$F NMR (471 MHz, acetone-d6) δ −60.15, −142.35 (q, J=48.6 Hz); $^{11}$B NMR (128 MHz, acetone-d6) δ 3.03 (q, J=50.4 Hz); HRMS (ESI-TOF) m/z calcd. for $C_8H_5BF_6Cl^-$ [M−K]$^−$ 261.0077. found 261.0075.

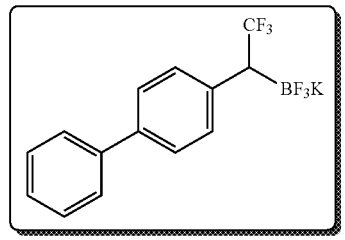

Potassium {1-[(1,1'-biphenyl)-4-yl]-2,2,2-trifluoroethyl}trifluoroborate (21)

Following the general procedure, starting from potassium 1,1'-biphenyltrifluoroborate (260 mg, 1 mmol), using CH$_2$Cl$_2$ (~1 M CF$_3$CHN$_2$, 2 mL) and p-tolylSiCl$_3$ (338 mg, 1.5 mmol), the product was obtained in the following manner: the crude was dissolved in a minimum of hot acetone and Et$_2$O was added to precipitate the unreacted 1,1'-biphenyltrifluoroborate starting material. The filtrate was evaporated, and the pure product was recrystallized from the resulting solid to provide the trifluoromethylated trifluoroborate as a white solid (222 mg, 65%): mp 158-162° C.; IR (neat) 1489, 1249, 1140, 1052, 997, 960, 828, 753, 695, 622 cm$^{-1}$; $^1$H NMR (500 MHz, acetone-d6) δ 7.67-7.59 (m, 2H), 7.49-7.36 (m, 6H), 7.30-7.28 (m, 1H), 2.55 (s, 1H); $^{13}$C NMR (126 MHz, acetone-d6) δ 141.5, 139.4, 137.7, 130.6, 130.3 (q, J=277.3 Hz), 128.8, 126.8, 126.8, 125.9, 44.1; $^{19}$F NMR (471 MHz, acetone-d6) δ −59.92, −141.94 (q, J=47.1 Hz); $^{11}$B NMR (128 MHz, acetone-d6) δ 3.23 (q, J=51.8 Hz); HRMS (ESI-TOF) m/z calcd. for $C_{14}H_{10}BF_6^-$ [M−K]$^−$ 303.0780. found 303.0781.

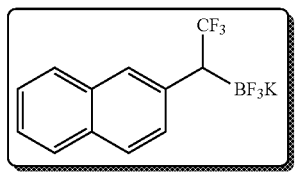

Potassium Trifluoro[2,2,2-trifluoro-1-(naphthalen-2-yl)ethyl]borate (2m)

Following the general procedure, starting from potassium 2-naphthyltrifluoroborate (234 mg, 1 mmol), using CH$_2$Cl$_2$ and TMS-Cl, the desired product was obtained as a white solid (278 mg, 88%) after sonicating in hexane; mp>250° C.; IR (neat) 1318, 1249, 1215, 1122, 1085, 1049, 1007, 966, 950, 849, 825, 758 cm$^{-1}$; $^1$H NMR (500 MHz, acetone-d6) δ 7.79-7.75 (m, 3H), 7.69 (d, J=8.5 Hz, 1H), 7.57 (d, J=8.5 Hz, 1H), 7.41-7.34 (m, 2H), 2.69 (s, 1H); $^{13}$C NMR (126 MHz, acetone-d6) δ 137.8, 133.8, 132.0, 130.4 (q, J=278.1 Hz), 129.4, 128.1, 127.5, 127.4, 126.5, 125.3, 124.6, 44.7; $^{19}$F NMR (471 MHz, acetone-d6) δ −59.83, −141.69 (q, J=48.6 Hz); $^{11}$B NMR (128 MHz, acetone-d6) δ 3.83 (q, J=51.2 Hz); HRMS (ESI-TOF) m/z calcd. for $C_{12}H_8BF_6^-$ [M−K]$^−$ 277.0623. found 277.0631.

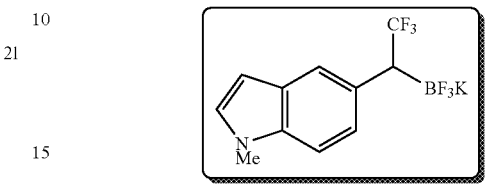

Potassium Trifluoro[2,2,2-trifluoro-1-(1-methyl-1H-indol-5-yl)ethyl]borate (2n)

Following the general procedure, starting from potassium 1-methyl-1H-indol-5-yltrifluoroborate (237 mg, 1 mmol), using CH$_2$Cl$_2$ and TMS-Cl, the desired product was obtained as a purple solid (287 mg, 90%) after sonicating in Et$_2$O; mp 185° C. (decomposes); IR (neat) 1494, 1253, 1129, 1096, 954, 863, 804, 731, 668, 649 cm$^{-1}$; $^1$H NMR (500 MHz, acetone-d6) δ 7.51 (s, 1H), 7.21 (d, J=8.4 Hz, 1H), 7.15 (d, J=8.5 Hz, 1H), 7.06 (d, J=3.0 Hz, 1H), 6.33-6.25 (m, 1H), 3.75 (s, 3H), 2.53 (s, 1H); $^{13}$C NMR (126 MHz, acetone-d6) δ 135.6, 130.8 (q, J=276.8 Hz), 129.8, 128.7, 128.5, 124.4, 121.9, 108.2, 100.2, 43.5, 32.0; $^{19}$F NMR (471 MHz, acetone-d6) δ −60.24, −141.46 (q, J=50.2 Hz); $^{11}$B NMR (128 MHz, acetone-d6) δ 4.01 (q, J=52.2 Hz); HRMS (ESI-TOF) m/z calcd. for $C_{11}H_9BNF_6^-$ [M−K]$^−$ 280.0732. found 280.0727.

IV. Synthesis of Polytrifluoromethylated Derivatives

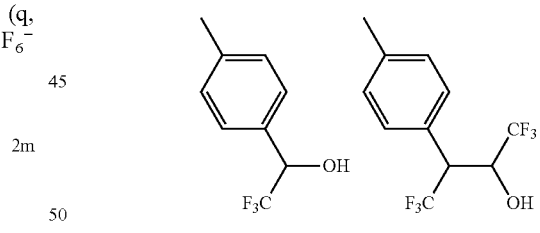

2,2,2-Trifluoro-1-(p-tolyl)ethanol and 1,1,1,4,4,4-hexafluoro-3-(p-tolyl)butan-2-ol Procedure E:

p-Tolylboronic acid (136 mg, 1 mmol) was added to a 20 mL Biotage microwave vial equipped with a stir bar. The vial was sealed and purged with argon three times. The diazo stock solution (8 mL, 0.5 M) was added, and the reaction was stirred at 40° C. overnight. The solvent was evaporated from the crude reaction mixture under reduced pressure, and the solid was redissolved in THF (5 mL), then treated with a solution of 2 N NaOH (6 M)/30% H$_2$O$_2$ (2:1 v/v, 2 mL) at 0° C. The reaction mixture was allowed to warm to RT and stirred for 2 h. The phases were separated, and the aqueous phase was extracted with Et$_2$O (2×5 mL). The organic phases were combined, dried (MgSO$_4$), concentrated, and purified by column chromatography to obtain 2,2,2-trifluoro-1-(p-tolyl)ethanol (43 mg, 40%) and 1,1,1,4,4,4-hexafluoro-3-(p-tolyl)butan-2-ol (40 mg, 21%) along with p-methylphenol (38 mg, 14%).

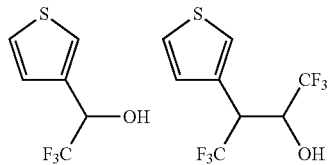

2,2,2-Trifluoro-1-(3-thienyl)ethanol and 1,1,1,4,4,4-hexafluoro-3-(3-thienyl)butan-2-ol Using procedure E, 2,2,2-trifluoro-1-(3-thienyl)ethanol was obtained as a yellow oil (33 mg, 18%) and 1,1,1,4,4,4-hexafluoro-3-(3-thienyl)butan-2-ol was obtained as a yellow oil (52 mg, 20%).

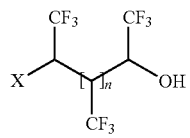

Procedure F (X=F or Ar/HetAr):

BF$_3$.Et$_2$O (0.5 M in CH$_2$Cl$_2$, 0.1 mL) was added to a solution of 2,2,2-trifluorodiazoethane (0.5 M in CH$_2$Cl$_2$, 10 mL) at 0° C. under Ar. The reaction mixture was heated to 40° C. overnight, then cooled to 0° C. and quenched with NaOH (6 M)/30% H$_2$O$_2$ (2:1 v/v, 0.5 mL) at 0° C. under Ar. The crude mixture was evaporated, then sonicated in water and filtered to eliminate the inorganic salts. GPC analysis of the light yellow solid obtained showed M$_W$ of ~5000, with a PDI=1.2.

Other initiators (3-thiophenyl-acid or p-tolylboronic acid) react with 10 to 100 equivalents of 2,2,2-trifluorodiazoethane in other solvents (ClCH$_2$CH$_2$Cl$_2$ or CHCl$_3$) at temperatures of RT, 40° C., and 60° C. The average molecular weights of the trifluoromethylated oligomers range between 800 and 5000.

An alternative scheme provides for the reactions of fluoroborate precursors with excess CF$_3$—CH=N$_2$ in the presence of fluorophiles to yield oligomeric or polymeric materials:

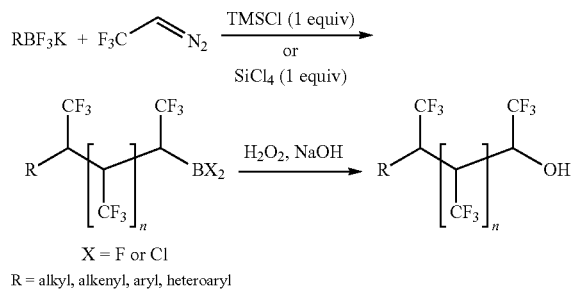

V. Oxidation of Trifluoromethylated Organoborons

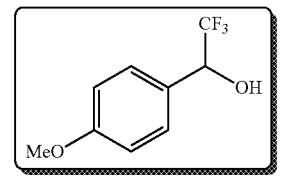

2,2,2-Trifluoro-1-(4-methoxyphenyl)ethan-1-ol (3a)

Potassium 4-methoxyphenyltrifluoroborate (107 mg, 0.5 mmol) was added into a 5 mL Biotage microwave vial equipped with a stir bar. The vial was sealed and purged with argon three times. A solution of CF$_3$CHN$_2$ in toluene (~0.5 M, 2 mL) was added under Ar, then freshly distilled p-tolyl-SiCl$_3$ (124 mg, 0.55 mmol) was added, and the reaction was stirred at 40° C. overnight. A solution of pinacol (65 mg, 0.55 mmol) in dry, degassed CH$_2$Cl$_2$ (1 mL) was then added under Ar, and the resulting mixture was stirred at RT for 1 h. The reaction was passed through a plug of Celite, then concentrated under vacuum. The resulting sticky oil was dissolved in toluene (5 mL), cooled to 0° C., then a solution of NaOH (3 M, 0.5 mL) and H$_2$O$_2$ (30%, 0.5 mL) were added dropwise. The reaction was stirred at RT overnight, then acidified by adding a solution of HCl (1 M) dropwise at 0° C. The crude was diluted with deionized H$_2$O (2 mL). The organic phase was extracted with Et$_2$O (3×5 mL), dried (MgSO$_4$), and concentrated under vacuum. The resulting crude mixture was purified on column chromatography using a gradient hexanes/EtOAc (100/0 to 90/10), to provide the desired alcohol as a colorless oil (78 mg, 75%). IR (neat) 3420, 1616, 1514, 1249, 1168, 1124, 1031, 818, 695 cm$^{-1}$; $^1$H NMR (500 MHz, CDCl$_3$) δ 7.38 (d, J=8.6 Hz, 2H), 6.92 (d, J=8.8 Hz, 2H), 4.93 (q, J=6.6 Hz, 1H), 3.81 (s, 3H), 2.93 (s, 1H); $^{13}$C NMR (126 MHz, CDCl$_3$) δ 160.6, 128.9, 126.4, 124.5 (q, J=281.9 Hz), 114.2, 72.6 (q, J=95.6 Hz), 55.4; $^{19}$F NMR (471 MHz, CDCl$_3$) δ −78.54; HRMS (ESI-TOF) m/z calcd. for C$_9$H$_9$F$_3$ 206.0555. found 206.0564.

VI. Bromination of Trifluoromethylated Organoborons

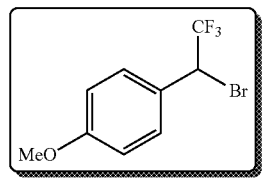

1-(1-Bromo-2,2,2-trifluoroethyl)-4-methoxybenzene

Potassium 4-methoxyphenyltrifluoroborate (107 mg, 0.5 mmol) was added into a 5 mL Biotage microwave vial equipped with a stir bar. The vial was sealed and purged with argon three times. A solution of CF$_3$CHN$_2$ in toluene (~0.5 M, 2 mL) was added under Ar, then freshly distilled p-tolyl- SiCl₃ (124 mg, 0.55 mmol) was added, and the reaction was stirred at 40° C. overnight. The reaction was diluted with CH₂Cl₂ (1 mL), then a solution of NBS (134 mg, 0.75 mmol) in MeCN (2 mL) was added slowly under Ar. The reaction was stirred at RT for 5 h, then passed though a plug of Celite and concentrated under vacuum. The crude mixture was purified by column chromatography using hexanes to provide the desired bromide as a colorless oil (68 mg, 51%). IR 1612, 1515, 1253, 1179, 1158, 1108, 1032, 822, 670 cm⁻¹; ¹H NMR (500 MHz, CDCl₃) δ 7.43 (d, J=8.7 Hz, 2H), 6.91 (d, J=8.8 Hz, 2H), 5.11 (q, J=7.4 Hz, 1H), 3.83 (s, 3H); ¹³C NMR (126 MHz, CDCl₃) δ 160.9, 130.6, 125.0, 123.58 (q, J=277.7 Hz), 114.4, 55.5, 47.2 (q, J=34.4 Hz); ¹⁹F NMR (471 MHz, CDCl₃) δ −70.63; HRMS (ESI-TOF) m/z calcd. for C₉H₈OF₃Br, 267.9711. found 267.0709.

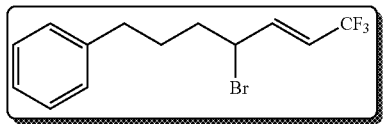

3c (E)-(4-Bromo-7,7,7-trifluorohept-5-en-1-yl)benzene (E)-(5-Phenylpent-1-enyl)trifluoroborate (126 mg, 0.5 mmol) was added into a 5 mL Biotage microwave vial equipped with a stir bar. The vial was sealed and purged with argon three times. A solution of CF₃CHN₂ in toluene (~0.5 M, 2 mL) was added under Ar, then freshly distilled p-tolyl-SiCl₃ (124 mg, 0.55 mmol) was added, and the reaction was stirred at 40° C. overnight. The reaction was allowed to cool to RT, then a solution of NBS (134 mg, 0.75 mmol) in MeCN (2 mL) was added under Ar. The reaction was stirred at RT for 5 h, then passed though a plug of Celite and concentrated under vacuum. The crude mixture was purified on silica gel column chromatography using pentane to provide the desired bromide as a colorless oil (93 mg, 60%). IR (neat) 1311, 1276, 1124, 752, 699 cm⁻¹; ¹H NMR (500 MHz, CDCl₃) δ 7.34-7.27 (m, 2H), 7.24-7.14 (m, 3H), 6.47-6.42 (m, 1H), 5.80-5.73 (m, 1H), 4.48-4.44 (m, 1H), 2.68-2.65 (m, 2H), 2.00-1.68 (m, 4H); ¹³C NMR (126 MHz, CDCl₃) δ 141.4, 139.8 (q, J=6.3 Hz), 128.6 (d, J=17.6 Hz), 126.3, 123.6, 121.5, 119.6 (q, J=34.4 Hz), 50.1, 37.5, 35.2, 29.2; ¹⁹F NMR (471 MHz, CDCl₃) δ −64.31; HRMS (ESI-TOF) m/z calcd. for C₁₃H₁₄F₆Br, 306.0231. found 306.0235.

VII. Chlorination of Trifluoromethylated Organoborons

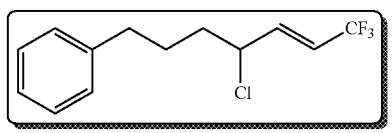

3d (E)-(4-Chloro-7,7,7-trifluorohept-5-en-1-yl)benzene (E)-(5-Phenylpent-1-enyl)trifluoroborate (126 mg, 0.5 mmol) was added into a 5 mL Biotage microwave vial equipped with a stir bar. The vial was sealed and purged with argon three times. The solution of CF₃CHN₂ in toluene (~0.5 M, 2 mL) was added under Ar, then freshly distilled p-tolyl-SiCl₃ (124 mg, 0.55 mmol) was added, and the reaction was stirred at 40° C. overnight. The reaction was allowed to cool to RT, then a solution of NCS (100 mg, 0.75 mmol) in MeCN (2 mL) was added under Ar. The reaction was stirred at RT for 5 h, then passed though a plug of Celite and concentrated under vacuum. The crude mixture was purified on silica gel column chromatography using pentane to provide the desired chloride as a pale yellow oil (80 mg, 61%). IR (neat) 1313, 1277, 1127, 968, 745, 700 cm⁻¹; ¹H NMR (500 MHz, CDCl₃) δ 7.31-7.28 (m, 2H), 7.22-7.17 (m, 3H), 6.41-6.33 (m, 1H), 5.89-5.83 (m, 1H), 4.45-4.36 (m, 1H), 2.69-2.64 (m, 2H), 1.91-1.83 (m, 3H), 1.79-1.71 (m, 1H); ¹³C NMR (126 MHz, CDCl₃) δ 141.5, 139.4 (q, J=6.3 Hz), 128.6 (d, J=16 Hz), 126.2, 123.8, 121.6, 120.1 (q, J=34.3 Hz), 59.0, 37.1, 35.2, 27.9; ¹⁹F NMR (471 MHz, CDCl₃) δ −64.30; HRMS (ESI-TOF) m/z calcd. for C₁₃H₁₄F₆Cl, 262.0736. found 262.0746.

VIII. Protodeboronation of Trifluoromethylated Organoborons

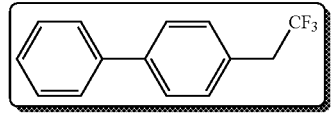

3e 4-(2,2,2-Trifluoroethyl)-1,1'-biphenyl

Potassium [1,1'-biphenyl]-4-yltrifluoroborate (130 mg, 0.5 mmol) was added into a 5 mL Biotage microwave vial equipped with a stir bar. The vial was sealed and purged with argon three times. A solution of CF₃CHN₂ in toluene (~1 M, 1 mL) was added under Ar, then freshly distilled TMSCl (124 mg, 1.1 mmol) was added under Ar, and the reaction was stirred at 40° C. overnight. A solution of pinacol (99 mg, 0.5 mmol) in CH₂Cl₂ (1 mL) was added under Ar at RT, and the reaction was stirred for 1 h. The mixture was passed through a plug a Celite and concentrated under vacuum. The crude was dissolved in toluene (5 mL), then TBAF.3H₂O (236 mg, 0.75 mmol) was added. After stirring at RT for 5 h, the reaction was diluted with deionized H₂O (5 mL). The organic phase was extracted with Et₂O (3×5 mL), dried (MgSO₄), and concentrated under vacuum. The resulting crude mixture was purified by column chromatography using pentane to provide the desired trifluoroethylated compound as a white solid (65 mg, 55%). mp 70-72° C.; IR (neat) 1363, 1250, 1143, 1072, 764, 736, 687 cm⁻¹; ¹H NMR (500 MHz, CDCl₃) δ 7.61-7.35 (m, 9H), 3.42 (q, J=10.8 Hz, 2H); ¹³C NMR (126 MHz, CDCl₃) δ 141.3, 140.7, 130.7, 129.3 (q, J=2.94 Hz), 129.0, 127.6, 127.5, 127.3, 125.9 (q, J=276.8 Hz), 40.1 (q, J=29.8 Hz); ¹⁹F NMR (471 MHz, CDCl₃) δ −65.85 (t, J=10.7 Hz); HRMS (ESI-TOF) m/z calcd. for C₁₄H₁₁F₃ 236.0813. found 236.0820.

A similar result has also been observed with protracted reaction times:

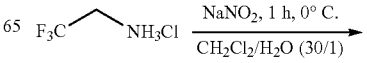

-continued

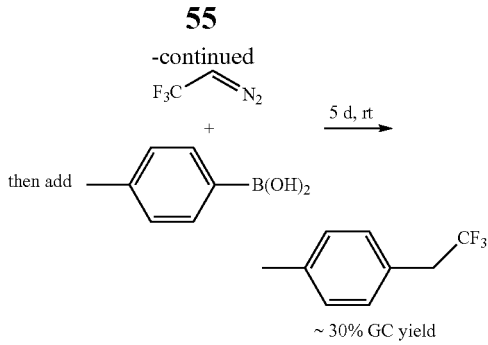

~30% GC yield

IX. Elimination of Trifluoromethylated Organoborons

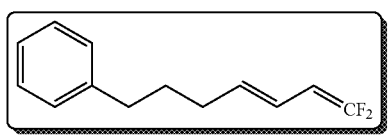

(E)-(7,7-Difluorohepta-4,6-dien-1-yl)benzene (E)-(5-Phenylpent-1-enyl)trifluoroborate (126 mg, 0.5 mmol) was added into a 5 mL Biotage microwave vial equipped with a stir bar. The vial was sealed and purged with argon three times. A solution of $CF_3CHN_2$ in toluene (~0.5 M, 1.5 mL) was added under Ar, then freshly distilled p-tolylSiCl$_3$ (124 mg, 0.55 mmol) was added, and the reaction was stirred at 40° C. overnight. The reaction was then stirred at 75° C. for 3 h, then passed through a plug of Celite, and concentrated under vacuum. The crude mixture was purified on silica gel chromatography using pentane to provide the desired diene as a colorless oil (83 mg, 80%). IR (neat) 2933, 1723, 1187, 965, 918, 744, 698 cm$^{-1}$; $^1$H NMR (500 MHz, CDCl$_3$) δ 7.33-7.26 (m, 2H), 7.18-7.17 (m, 3H), 5.95-5.89 (m, 1H), 5.65-5.59 (m, 1H), 4.95-4.87 (m, 1H), 2.65-2.59 (m, 2H), 2.15-2.10 (m, 2H), 1.76-1.69 (m, 2H); $^{13}$C NMR (126 MHz, CDCl$_3$) δ 156.1 (dd, J=289, 289 Hz), 142.4, 133.2 (dd, J=3.8, 2.5 Hz), 128.6, 128.5, 125.9, 119.2 (dd, J=1.3, 1.3 Hz), 82.1 (dd, J=16.4, 17.6 Hz), 35.5, 32.5, 31.0; $^{19}$F NMR (471 MHz, CDCl$_3$) δ −87.70 (d, J=34.7 Hz), −90.38 (d, J=34.6 Hz); HRMS (ESI-TOF) m/z calcd. for $C_{13}H_{14}F_2$ 208.1064. found 208.1066.

X. Reaction of Trifluoromethylated Organoborons with Ethyl Diazoacetate

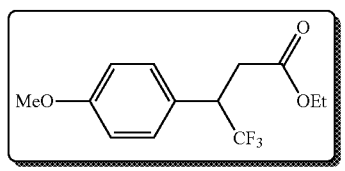

3g

Ethyl 4,4,4-Trifluoro-3-(4-methoxyphenyl)butanoate

Potassium 4-methoxyphenyltrifluoroborate (107 mg, 0.5 mmol) was added into a 5 mL Biotage microwave vial equipped with a stir bar. The vial was sealed and purged with argon three times. A solution of $CF_3CHN_2$ in toluene (~0.5 M, 2 mL) was added under Ar, then freshly distilled p-tolylSiCl$_3$ (124 mg, 0.55 mmol) was added, and the reaction was stirred at 40° C. overnight. The reaction was allowed to cool to RT, then $N_2CHCO_2Et$ (173 mg, 1.5 mmol) was added under Ar, and the reaction was stirred at 60° C. for 48 h. The reaction was cooled to 0° C. and quenched by a dropwise addition of a saturated solution of NH$_4$Cl (2 mL). Deionized H$_2$O (5 mL) was added, then the organic phase was extracted with Et$_2$O (3×5 mL), dried over MgSO$_4$, and concentrated under vacuum. The crude mixture was purified by column chromatography using a gradient of hexane/EtOAc (100/0 to 98/2) to provide the desired compound as a colorless oil (60 mg, 43%). IR (neat) 1739, 1516, 1304, 1248, 1153, 1117, 1105, 1033, 967, 829 cm$^{-1}$; $^1$H NMR (500 MHz, CDCl$_3$) δ 7.24 (d, J=8.7 Hz, 2H), 6.88 (d, J=8.8 Hz, 2H), 4.11-4.00 (m, 2H), 3.88-3.83 (m, 1H), 3.80 (s, 3H), 2.99 (dd, J=16.1, 5.0 Hz, 1H), 2.84 (dd, J=16.1, 10.0 Hz, 1H), 1.14 (t, J=7.1 Hz, 3H); $^{13}$C NMR (126 MHz, CDCl$_3$) δ 170.2, 159.8, 130.1, 126.6 (q, J=279.4 Hz), 125.8, 114.2, 61.1, 55.4, 45.6 (q, J=27.7 Hz), 34.7, 14.1; $^{19}$F NMR (282 MHz, CDCl$_3$) δ −70.60 (d, J=9.2 Hz); HRMS (ESI-TOF) m/z calcd. for $C_{13}H_{15}O_3F_3$ 277.1052. found 277.1052.

XII. Reaction of Organoborate Esters with Dihaloalkanes

An experiment was conducted according to the following scheme, resulting in the designated product isolated in 41% yield. The reaction is believed to have general applicability for the addition of dihaloalkanes to other aryl and heteroaryl compounds.

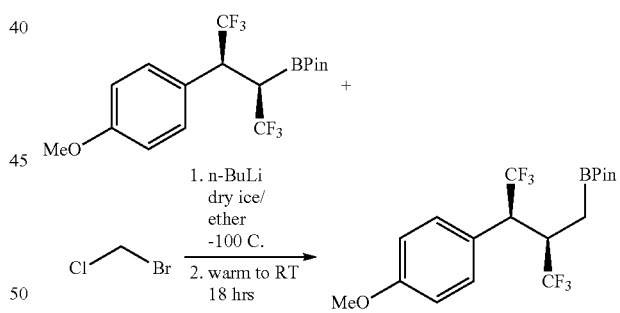

XIII. Exemplary Cross Coupling Reactions

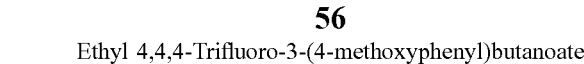

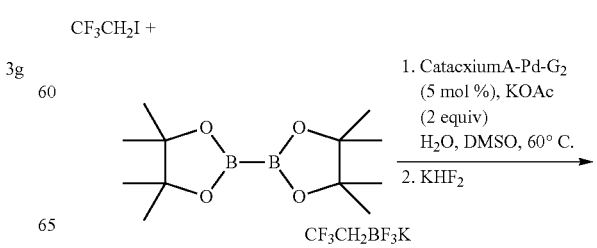

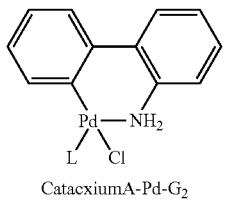
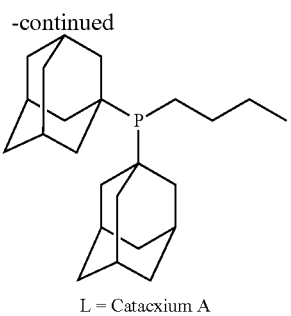

CatacxiumA-Pd-G$_2$

L = Catacxium A

Synthesis of potassium 2,2,2-trifluoroethyltrifluoroborate

Figure 7:
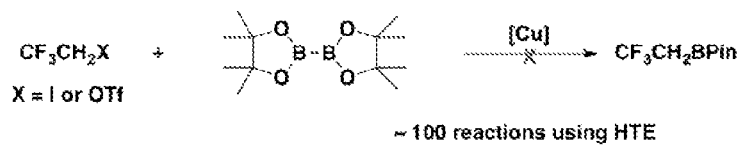
FIG. 7 provides schemes for the preparation of 2,2,2-trifluoroethyltrifluoroborate via metal-catalyzed borylation
Figure 7:
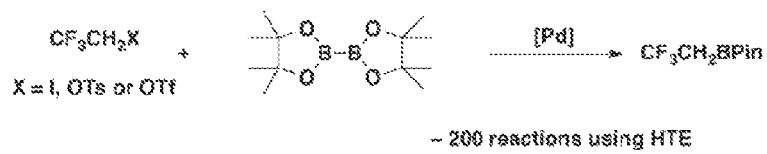
Figure 7:
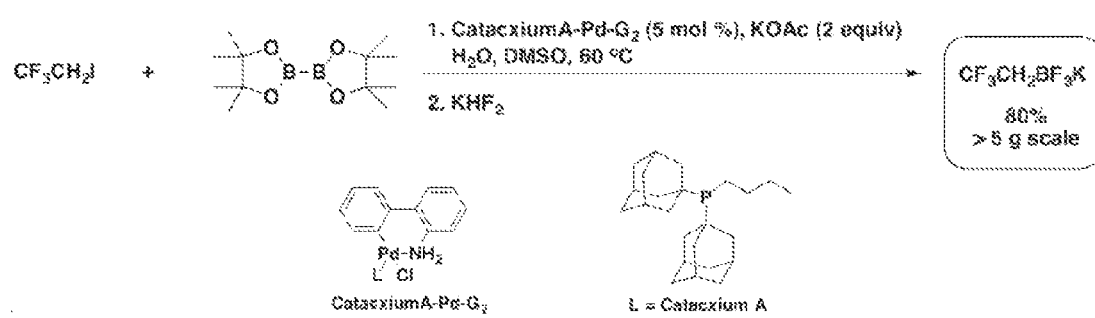

See FIG. 7. An oven-dried 20 mL microwave vial equipped with a stirrer bar was charged with bis(pinacolato)diboron (1.282 g, 4.8 mmol), dry KOAc (784 mg, 8 mmol), and CatacxiumA-Pd-G2 (133 mg, 0.2 mmol) and then sealed a disposable PTFE septum. The vial was then evacuated under vacuum and purged with Ar three times. Dry, degassed DMSO (10 mL) was added via syringe under Ar. 2,2,2-Trifluoroethyliodide (840 mg, 4 mmol) was then added via syringe and the reaction mixture was stirred at 60° C. overnight. The crude mixture was distilled under reduced pressure, to remove the salts. The distilled crude mixture was quenched with a saturated solution of KHF$_2$ (~4.5M, 10 mL) at 0° C., and the solvents were evaporated off by distillation. The crude was then extracted in dry acetone (2×20 mL). The product was recrystallized in using acetone/hexane/Et$_2$O to provide the pure CF$_3$CH$_2$BF$_3$K as a white solid (592 mg, 78%). $^1$H NMR (500 MHz, acetone-d$_6$) δ 1.04 (s, 2H); $^{13}$C NMR (126 MHz, acetone-d$_6$) δ 130.96 (q, J=92.7 Hz), 24.22; $^{19}$F NMR (471 MHz, Acetone) δ −56.23, −139.01 (q, J=51.8 Hz); $^{11}$B NMR (128 MHz, acetone-d$_6$) δ 2.65 (q, J=51.3 Hz); HRMS (ESI-TOF) m/z calcd. for C$_2$H$_2$BF$_6$ 151.0154. found 151.0190.

The compound, CF$_3$CH$_2$BF$_3$K, and its method of synthesis and use are considered within the scope of the present invention. Similarly, compounds of the general formula R$_f$"—CH$_2$—Y, where R$_f$" is a perfluorinated alkyl, aryl, or heteroaryl and Y is BPin, BF$_3$K, or BF$_3$N(n-Bu)$_4$, and their methods of making, analogous to that used to prepare CF$_3$CH$_2$BF$_3$K, and using are similarly considered within the scope of the invention.

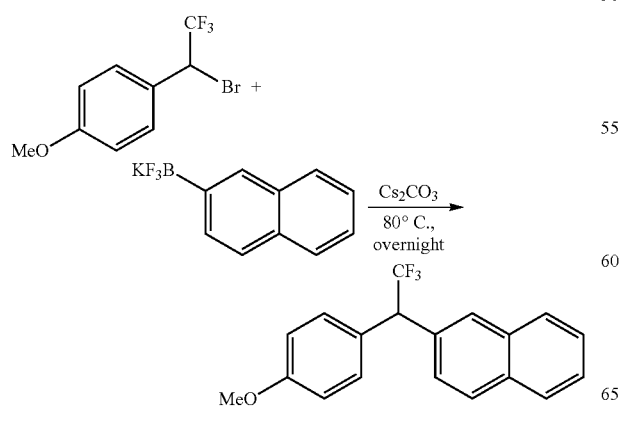

Preparation of 2-(2,2,2-trifluoro-1-(4-methoxyphenyl)ethyl)naphthalene

An oven-dried 20 mL microwave vial equipped with a stirrer bar was charged with potassium trifluoro(naphthalen-2-yl)borate (0.246 g, 1.05 mmol), Cs$_2$CO$_3$ (1.30 g, 4 mmol), Pd$_2$dba$_3$ (0.025 mmol, 2.5 mol %) and CataXciumPtB (28.7 mg, 0.1 mmol) and then sealed a disposable PTFE septum. The vial was then evacuated under vacuum and purged with Ar three times. Dry, degassed t-BuOH (8 mL) and H$_2$O (2 mL) were added via syringe under Ar. 1-(1-Bromo-2,2,2-trifluoroethyl)-4-methoxybenzene (0.269 g, 1 mmol) was then added via syringe, and the reaction mixture was stirred at 80° C. for 24 h. The mixture was then cooled to rt and diluted with brine (5 mL). The reaction mixture was extracted with CH$_2$Cl$_2$ (4×5 mL). The combined organic phases were dried over MgSO$_4$, filtered, and then concentrated in vacuo. The crude mixture was purified by column chromatography (hexane/ethyl acetate 98:2) to provide the desired product as a colorless oil (203 mg, 63%). $^1$H NMR (CDCl$_3$, 500 MHz): δ 7.89 (s, 1H), 7.84 (m, 3H), 7.50 (m, 2H), 7.44 (d, J=8.5 Hz, 1H), 7.34 (d, J=8.5 Hz, 2H), 6.90 (d, J=8.5 Hz, 2H), 4.83 (q, J=10 Hz, 1H), 3.80 (s, 3H); $^{13}$C NMR (CDCl$_3$, 125 MHz): δ 159.37, 133.35, 133.25, 132.79, 130.50, 128.57, 128.20, 128.08, 127.72, 127.57, 126.86, 126.54, 126.51 (q, J=279 Hz), 126.50, 114.24, 55.35, 54.95 (q, =28 Hz); $^{19}$F NMR (CDCl$_3$, 470 MHz): δ −65.83 (s, 3F); IR (neat)=2932, 2361, 1611, 1514, 1250, 1153, 1101, 1034, 816, 746 cm-1; HRMS (CI) calcd. for C$_{19}$H$_{15}$F$_3$O (MH$^+$), 317.1153. found 317.1176.

As those skilled in the art will appreciate, numerous modifications and variations of the present invention are possible in light of these teachings, and all such are contemplated hereby. For example, in addition to the embodiments described herein, the present invention contemplates and claims those inventions resulting from the combination of features of the invention cited herein and those of the cited prior art references which complement the features of the present invention. Similarly, those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true spirit and scope of the invention.

The disclosures of each patent, patent application, and publication cited or described in this document are hereby incorporated herein by reference, each in its entirety, for all purposes.

What is claimed:
1. A compound of Formula Ia:

wherein
n is an integer from 1 to 50;
X is optionally substituted C$_{2-20}$alkyl; optionally substituted C$_{1-20}$heteroalkyl; optionally substituted C$_{2-20}$alkenyl; optionally substituted C$_{2-20}$alkynyl; optionally substituted cycloalkyl, optionally substituted heterocycloalkyl, optionally substituted aryl, optionally substituted heteroaryl, or fluorine; and Y is —B-pinacol; —B(OR)$_2$; —BF$_3$K; or BZ$_2$;

wherein each R is independently H or C$_{1-6}$alkyl; and Z is halogen.

2. The compound of claim 1, wherein n is 1 to 5.

3. The compound of claim 1, wherein n is 6 to 10.

4. The compound of claim 1, wherein n is 11 to 50.

5. The compound of claim 1, wherein n is 1 or 2.

6. The compound of claim 1, wherein n is 1.

7. The compound of claim 1, wherein X is optionally substituted aryl.

8. The compound of claim 7, wherein the aryl is optionally substituted phenyl, naphthyl, or fluorenyl.

9. The compound of claim 7, wherein the aryl is substituted with 1, 2, or 3 substitutents independently selected from the group consisting of C$_{1-6}$alkyl; C$_{1-6}$alkenyl; C$_{1-6}$alkynyl, —OC$_{1-6}$alkyl; —OC$_{1-6}$alkenyl; —C(O)C$_{1-6}$alkyl; —C(O)-aryl; —C(O)-heteroaryl; —C(O)OC$_{1-6}$alkyl; —C(O)O-aryl; —C(O)O-heteroaryl; —OC(O)C$_{1-6}$alkyl; —OC(O)-aryl; —OC(O)-heteroaryl; aryl; heteroaryl; halogen; haloalkyl; nitro, —OH, —CN; or —SO$_2$N(R$^1$)$_2$, wherein each R$^1$ is independently H or —C$_{1-6}$alkyl.

10. The compound of claim 1, wherein X is:

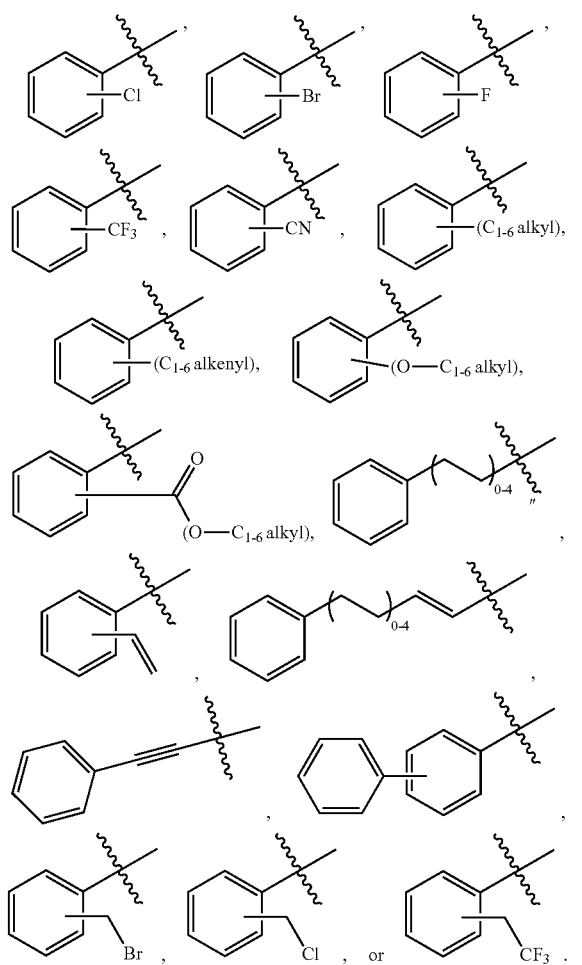

11. The compound of claim 1, wherein X is optionally substituted heteroaryl.

12. The compound of claim 11, wherein the heteroaryl is furanyl, imidazolyl, pyrrolidinyl, pyrimidinyl, tetrazolyl, thienyl, pyridyl, pyrrolyl, N-methylpyrrolyl, quinolinyl, or isoquinolinyl.

13. The compound of claim 11, wherein the heteroaryl is substituted with 1, 2, or 3 substitutents independently selected from the group consisting of C$_{1-6}$alkyl; —C$_{1-6}$alkenyl; —OC$_{1-6}$alkyl; —OC$_{1-6}$alkenyl; —C(O)C$_{1-6}$alkyl; —C(O)-aryl; —C(O)-heteroaryl; —C(O)OC$_{1-6}$alkyl; —C(O)O-aryl; —C(O)O-heteroaryl; —OC(O)C$_{1-6}$alkyl; —OC(O)-aryl; —OC(O)-heteroaryl; aryl; heteroaryl; halogen; haloalkyl; nitro, —OH; —CN; or —SO$_2$N(R$^1$)$_2$, wherein each R$^1$ is independently H or —C$_{1-6}$alkyl.

14. The compound of claim 11, wherein X is:

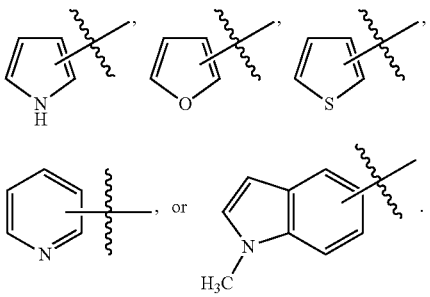

15. The compound of claim 1, wherein n is 1 or 2.

16. The compound of claim 1, wherein n is 3 to 50.

17. The compound of claim 1 that is selected from the group consisting of:

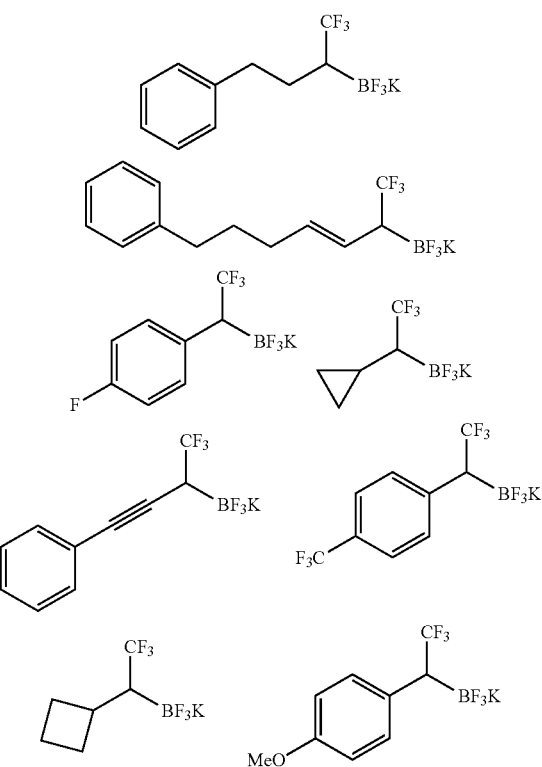

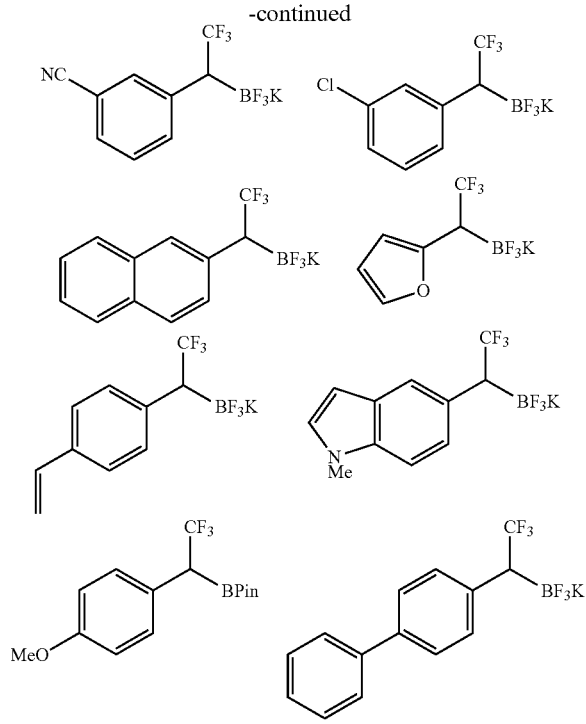
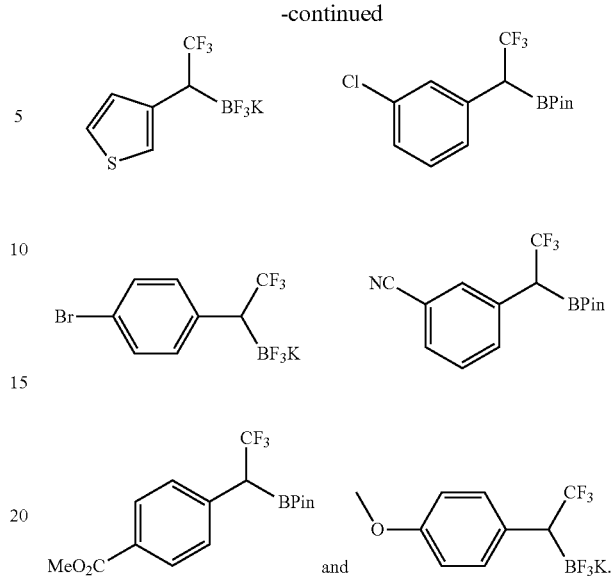
18. The compound of claim 1 that is an isolated compound.
* * * * *